United States Patent
Kem et al.

(10) Patent No.: US 9,150,558 B2
(45) Date of Patent: Oct. 6, 2015

(54) NICOTINE RECEPTOR TARGETED COMPOUNDS AND COMPOSITIONS

(71) Applicant: University of Florida Research Foundation, Gainesville, FL (US)

(72) Inventors: William R. Kem, Gainesville, FL (US); Ferenc Soti, Gainesville, FL (US); Hong Xing, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 14/364,499

(22) PCT Filed: Dec. 11, 2012

(86) PCT No.: PCT/US2012/068943
§ 371 (c)(1),
(2) Date: Jun. 11, 2014

(87) PCT Pub. No.: WO2013/090260
PCT Pub. Date: Jun. 20, 2013

(65) Prior Publication Data
US 2014/0343042 A1    Nov. 20, 2014

Related U.S. Application Data

(60) Provisional application No. 61/569,539, filed on Dec. 12, 2011.

(51) Int. Cl.
| | | |
|---|---|---|
| *C07D 221/22* | (2006.01) | |
| *A61K 31/439* | (2006.01) | |
| *C07D 409/14* | (2006.01) | |
| *C07D 401/04* | (2006.01) | |
| *C07D 401/14* | (2006.01) | |
| *C07D 405/14* | (2006.01) | |

(52) U.S. Cl.
CPC ............ *C07D 409/14* (2013.01); *C07D 401/04* (2013.01); *C07D 401/14* (2013.01); *C07D 405/14* (2013.01)

(58) Field of Classification Search
CPC ............................ C07D 221/22; A61K 31/439
USPC .......................................... 546/112; 514/299
See application file for complete search history.

(56) References Cited

U.S. PATENT DOCUMENTS 6,448,286 B1 * 9/2002 Hansen et al. ............... 514/426

FOREIGN PATENT DOCUMENTS

| WO | WO-9201688 A1 | 2/1992 |
| WO | WO-0123385 A2 | 4/2001 |
| WO | WO-2008095944 A1 | 8/2008 |

OTHER PUBLICATIONS

Slavov, Svetoslav H., et al.: "A computational study of the bonding of 3-(arylidene) anabaseines to two major brain nicotinic acetylcholine receptors and to the acetylcholine binding protein"; European Journal of Medicinal Chemistry; Jun. 2010, pp. 2433-2446.
Hashimoto, Kenji, et al.; "α7 Nicotinic Receptor Agonists as Potential Therapeutic Drugs for Schizophrenia"; Current Medicinal Chemistry-Central Nervous System Agents., Sep. 2005, pp. 171-184.
Belluardo, Natale, et al.; "Central nicotinic receptors, neurotrophic factors and neuroprotection"; Behavioural Brain Research, Aug. 2000, pp. 21-34.
Hoepping, Alexander et al., Novel Conformationally Constrained Tropane Analogues by 6-endo-trig Radical Cyclization and Stille Coupling—Switch of Activity toward the Serotonin and/or Norepinephrine Transporter, Journal of Medicinal Chemistry; May 18, 2000, pp. 2064-2071.
International Search Report for PCT/US2012/068943 dated Mar. 29, 2013.

* cited by examiner

*Primary Examiner* — Niloofar Rahmani
(74) *Attorney, Agent, or Firm* — Locke Lord LLP; Jeffrey D. Hsi; Stephen W. Rafferty

(57) ABSTRACT

The invention relates to the design and synthesis of novel anabaseine-based compounds, which are useful in treating or preventing a wide variety of conditions, including nervous system diseases or disorders, such as, schizophrenia, Alzheimer's disease, Parkinson's disease, drug dependence, and substance addiction, and compositions, kits, and methods thereof. The invention also provides novel anabaseine-based compounds, compositions, kits, and methods thereof for treating or preventing non-nerve system diseases or disorders (such as, inflammation and cancer) in a subject identified in need thereof. Certain enantiomeric compounds of the invention exhibited enhanced selectivity toward α7 nAChRs relative to alpha4beta2 nAChRs. Other enantiomeric compounds of the invention exhibited enhanced selectivity for alpha4beta2 nAChRs relative to α7 nAChRs.

14 Claims, 5 Drawing Sheets

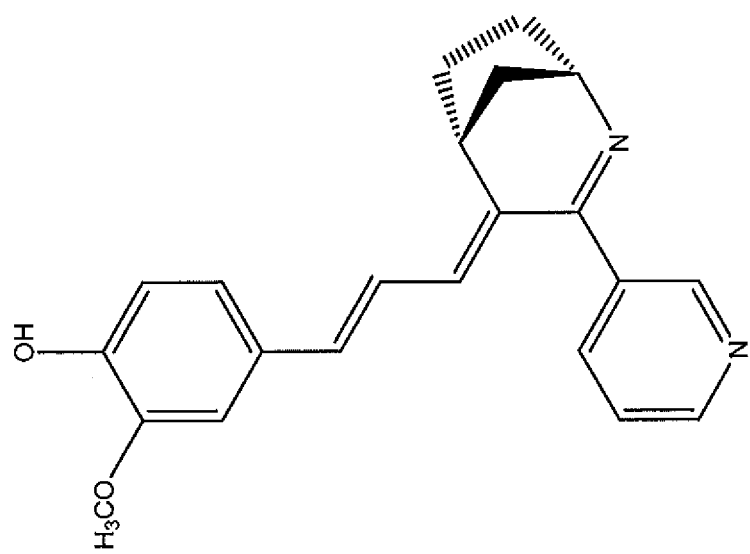
Figure 1. 3-(4-Hydroxy-3-methoxycinnamylidene)-4(R),6(S)-ethyleneanabaseine

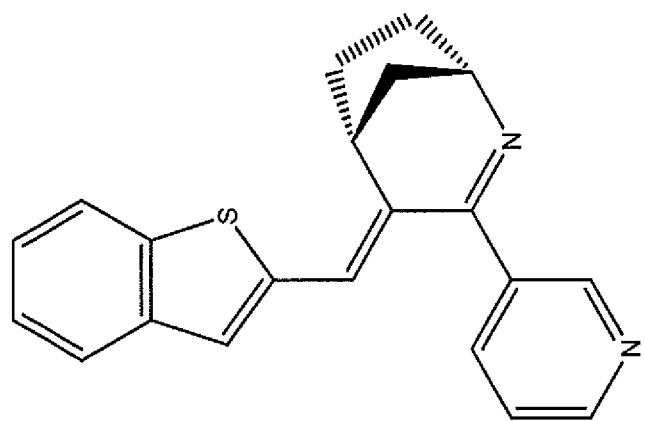
Figure 2. 3-(Benzo[b]thiophen-2-ylidene)-4(R),6(S)-ethyleneanabaseine

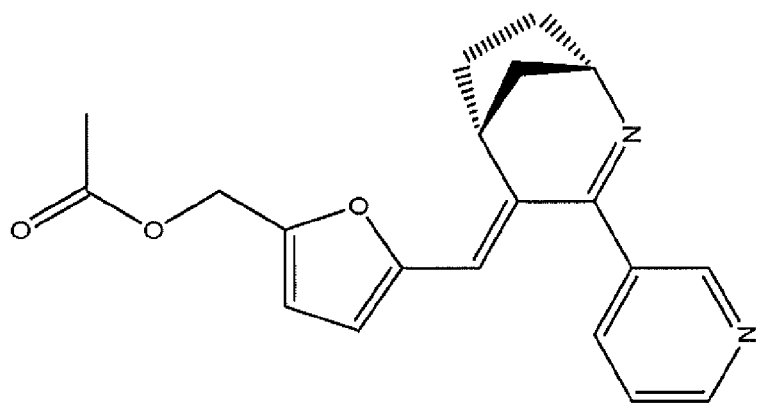
Figure 3. 3-(5-Acetoxyfurfurylidene)-4(R),6(S)-ethyleneanabaseine

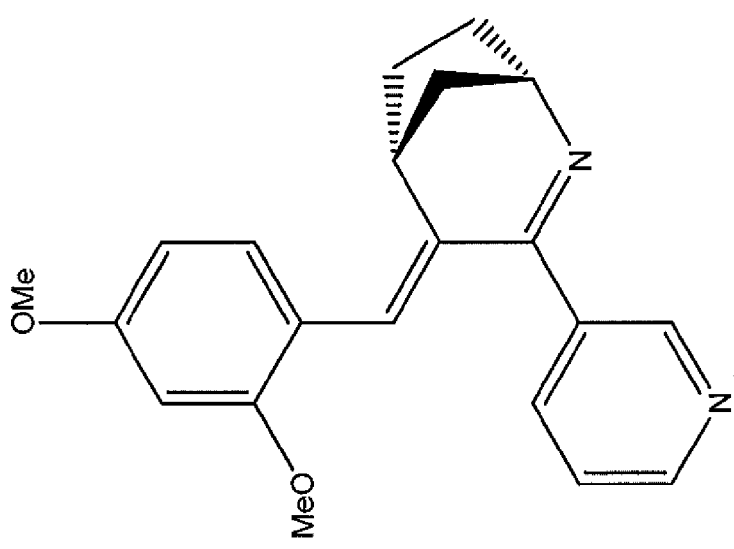
Figure 4. (1S,5R,E)-4-(2,4-dimethoxybenzylidene)-3-(pyridin-3-yl)-2-azabicyclo[3.2.1]oct-2-ene ("3-(DMXB)-4(R), 6(S)-EA")

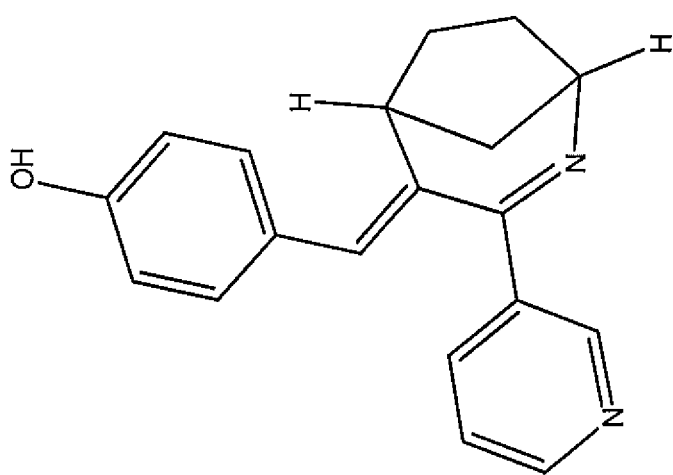
Figure 5. dl-3-(4-Hydroxybenzylidene)-4,6-ethyleneanabaseine

NICOTINE RECEPTOR TARGETED COMPOUNDS AND COMPOSITIONS

RELATED APPLICATIONS

This application is the U.S. National Stage, pursuant to 35 U.S.C. §371, of U.S. International Application No. PCT/US2012/068943, filed Dec. 11, 2012, designating the United States and published on Jun. 20, 2013 as Publication WO 2013/090260, which claims the benefit of U.S. provisional application No. 61/569,539, filed on Dec. 12, 2011. The entire teaching of the afore-mentioned applications are incorporated herein by reference.

STATEMENT OF RIGHTS TO INVENTIONS MADE UNDER FEDERALLY SPONSORED RESEARCH

This work was supported in part by National Institutes of Health NIMH Grant Nos. 5RO1MH061412-09 and 1P50MH086383. The government has certain rights in the invention.

BACKGROUND OF THE INVENTION

Acetylcholine receptors can be divided into muscarinic (mAChR) and nicotinic (nAChR) subtypes in the mammalian central nervous system (CNS). These subtypes are distinguished based on their ability to be stimulated by either the mushroom toxin muscarine or the plant alkaloid nicotine. Nicotinic receptors are important in cholinergic transmission in autonomic ganglia, striated muscles, the neuromuscular junction, and in brain and spinal synapses.

Several types of nicotinic acetylcholine receptors (nAChRs) are known to play a role in central nervous system activity, such as, they are involved in cognition, mood and neuroprotection. The various types of known nicotinic ligands appear to have different combinations of effects on nicotine-modulated functions, depending on the subtypes of nAChRs affected, some affecting all receptors, others having more selective actions. Within the nervous system, the non-neuronal cells include microglia and astrocytes; outside the nervous system non-neuronal cells expressing alpha7 receptors include macrophages, vascular endothelium and pulmonary epithelial cells. Some nAChRs are also expressed in non-neuronal or muscle cells.

All known mammalian nAChRs are cation selective ligand-gated ion channels that form pentameric structures in the plasma membrane. Each subunit of the pentamer contains four transmembrane domains. There are at least seventeen different nAChR subunit genes, including five found in striated muscle ($\alpha 1$, $\beta 1$, $\gamma$, $\delta$, $\epsilon$) and twelve neuronal nAChR subunits ($\alpha 2$-10, $\beta 2$-4). These channels can be composed of a number of different combinations of subunits.

Neuronal nAChR deficits have been implicated in several diseases including AD and schizophrenia. Until recently, the study of neurodegenerative diseases focused on the muscarinic type neuronal acetylcholine receptor (mAChR) because of its abundance in the brain when compared to the population of neuronal nicotinic receptors (nAChRs). However, the discovery of a greater relative loss of nicotinic receptors than of muscarinic receptors in the Alzheimer's brain, as well as evidence that nicotinic agonists enhance cognition has spurred interest in nAChRs. This is supported by the observation of enhanced attentiveness and rapid information processing in humans receiving nicotine or 3-(2,4-dimethoxy benzylidene)-anabaseine (DMXBA) (GTS-21) treatment.

The two major brain nAChRs $\alpha 4\beta 2$ ("alpha4beta2") and $\alpha 7$ ("alpha7") are important for cognitive processes such as attention, learning and memory. Since brain alpha7 nicotinic receptors are spared relative to the $\alpha 4\beta 2$ nAChRs in Alzheimer's disease and also possess exceptionally high calcium ion permeability, they are considered a particularly promising therapeutic target for treatment of Alzheimer's disease. In addition to their direct involvement in synaptic transmission, certain nicotinic receptor subtypes, particularly alpha7, because of their very high calcium permeability also stimulate calcium-dependent intracellular signal transduction processes that are neuroprotective by maintaining neuronal integrity in the presence of stressful states such as ischemia or mechanical trauma.

Central cholinergic neurons have been implicated in a number of neurodegenerative conditions including, Alzheimer's disease (AD) and schizophrenia. Alzheimer's disease (AD) affects an estimated 15 million people worldwide and accounts for approximately 50-60% of the overall cases of dementia for people over the age of 65. The characteristic pathology of AD includes extracellular $\beta$-amyloid plaques, intracellular neurofibrillary tangles, loss of neuronal synapes and pyramidal cells. The cholinergic dysfunction in AD is represented by a reduction in the activity of the ACh-synthesizing enzyme cholineactyltransferase (ChAT) and a loss in functional nAChRs. The cause(s) of this loss in cholinergic function is not yet known.

In schizophrenia, there is a disruption in the normal brain neuronal circuits that are responsible for filtering out responses to repetitive stimuli. This malfunction causes an overload of stimuli, which may lead to misperceptions of environmental stimuli in the form of delusions and hallucinations or withdrawal from environmental stimuli, causing schizoid behavior.

Small molecule compounds, for example, certain 3-arylidene-anabaseines, have been prepared (see, e.g., WO 2004/019943) for potential use in treating neurodegenerative diseases, and particularly with the hope that some compounds would bind to nicotinic $\alpha 7$ receptors. While many of the arylidene-anabaseines do selectively activate $\alpha 7$ receptors, these compounds also bind to other nicotinic receptors. For example, these arylidene-anabaseines also have antagonistic effects on brain $\alpha 4\beta 2$ subtype nicotinic receptors, which also participate in cognitive processes, and to a lesser extent other nicotinic receptor subtypes.

The importance of developing highly selective $\alpha 7$ nicotinic receptor agonists has increased as the role of these receptors in degenerative disease becomes clearer. There is a particular need for new compounds useful in treating cognitive dysfunctions (such as AD and schizophrenia) where degenerative processes drastically interfere with cognitive and physiological processes.

Therefore, there is a need for development of selective $\alpha 7$ agonists that do not bind to and interfere with the normal functioning of other nAChRs. Such agonists would produce fewer side effects arising from interaction with other nicotinic receptor subtypes.

SUMMARY OF THE INVENTION

One aspect of the invention provides a compound of Formula (I):

Formula (I)

[Structure of Formula (I)]

wherein
------, independently, stands for a single bond or a double bond;
$R^1$, on each occurrence, independently is $(C_1-C_3)$alkyl, hydroxy$(C_1-C_3)$alkyl, $(C_1-C_3)$alkoxy, cyano, halogen, aryl-O—, aryl, or a 5- to 6-membered heteroaryl; or two $R^1$ groups, together with the bonds they are attached to, form a 5 to 8 membered cyclic ring;
n is 0, 1, 2, 3, or 4;
Each of a1, a2, and a3 is 0 or 1, wherein two of a1, a2, and a3 are 0, and the other is 1;
$R^2$ is hydrogen, $(C_1-C_3)$alkyl, hydroxy$(C_1-C_3)$alkyl, or $(C_1-C_3)$alkoxy;
E and G, each independently, are absent, -hetero$(C_0-C_3)$alkyl-, $(C_1-C_3)$alkylene, or $(C_2-C_3)$alkenylene, wherein E and G cannot be both absent at the same time;
A is a bond or

[Structure of A group]

n' is 0, 1, or 2;
$R^4$ and $R^5$, on each occurrence, independently are hydrogen, $(C_1-C_3)$alkyl, hydroxy$(C_1-C_3)$alkyl, or $(C_1-C_3)$alkoxy;
X is aryl or heteroaryl, wherein said aryl and said heteroaryl are optionally substituted by one to five $R^3$ groups and/or one $R^c$ group;
$R^3$, on each occurrence, independently is hydrogen, halogen, $(C_1-C_3)$alkyl-C(O)O—, $(C_1-C_3)$alkyl-C(O)—, $(C_1-C_3)$alkyl-C(O)N($R^6$), N($R^6$)$_2$—, ($R^6$)$_2$NC(O)—, ($R^6$)$_2$N($C_1-C_5$)alkoxy, ($R^6$)$_3$N$^\oplus$ ($C_1-C_5$) alkoxy, hydroxyl, cyano, a sugar moiety or derivative thereof, $(C_1-C_3)$alkoxy optionally substituted by one or more same or different halogen or thio groups, or $(C_1-C_3)$alkyl optionally substituted by one or more same or different halogen or hydroxyl groups;
$R^6$, on each occurrence, independently is hydrogen, $(C_1-C_3)$alkyl, hydroxy$(C_1-C_3)$alkyl, or $(C_1-C_3)$alkoxy;
$R^a$ on each occurrence, independently is hydrogen, $(C_1-C_3)$alkyl, hydroxy$(C_1-C_3)$alkyl, $(C_1-C_3)$alkoxy, cyano, halogen, aryl, or aryl-O—;
$R^c$ is hydrogen, $(C_1-C_5)$alkoxy, or $(C_1-C_5)$alkyl, wherein said $(C_1-C_5)$alkoxy and said $(C_1-C_5)$alkyl are optionally substituted by one or more same or different substituents selected from the group of hydroxyl, $(C_1-C_3)$alkoxy, halogen, and thio; and
b is 0, 1, 2, 3, or 4;
or a pharmaceutically acceptable salt, solvate, hydrate, clathrate, polymorph, stereoisomer, enantiomer, or combination thereof.

In one embodiment, the invention provides a compound of Formula (IA):

[Structure of Formula (IA)]

Formula (IA)
wherein
------ independently, stands for a single bond or a double bond;
$R^1$, on each occurrence, independently is $(C_1-C_3)$alkyl, hydroxy$(C_1-C_3)$alkyl, $(C_1-C_3)$alkoxy, cyano, halogen, aryl-O—, aryl, or a 5- to 6-membered heteroaryl; or two R' groups, together with the bonds they are attached to, form a 5 to 8 membered cyclic ring;
n is 0, 1, 2, 3, or 4;
$R^2$ is hydrogen, $(C_1-C_3)$alkyl, hydroxy$(C_1-C_3)$alkyl, or $(C_1-C_3)$alkoxy;
E and G, each independently, are absent, -hetero$(C_0-C_3)$alkyl-, $(C_1-C_3)$alkylene, or $(C_2-C_3)$alkenylene, wherein E and G cannot be both absent at the same time;
A is a bond or

[Structure of A group]

n' is 0 or 1;
$R^4$ and $R^5$, on each occurrence, independently are hydrogen, $(C_1-C_3)$alkyl, hydroxy$(C_1-C_3)$alkyl, or $(C_1-C_3)$alkoxy;
X is aryl or heteroaryl, wherein said aryl and said heteroaryl are optionally substituted by one to five $R^3$ groups and/or one $R^c$ group;
$R^3$, on each occurrence, independently is hydrogen, halogen, $(C_1-C_3)$alkyl-C(O)O—, $(C_1-C_3)$alkyl-C(O)N($R^6$), N($R^6$)$_2$—, ($R^6$)$_2$NC(O)—, ($R^6$)$_2$N($C_1-C_5$)alkoxy, ($R^6$)$_3$N$^\oplus$ ($C_1-C_5$) alkoxy, hydroxyl, a sugar moiety or derivative thereof, $(C_1-C_3)$alkoxy optionally substituted by one or more same or different halogen or thio groups, or $(C_1-C_3)$alkyl optionally substituted by one or more same or different halogen or hydroxyl groups; and
$R^6$, on each occurrence, independently is hydrogen, $(C_1-C_3)$alkyl, hydroxy$(C_1-C_3)$alkyl, or $(C_1-C_3)$alkoxy;
$R^a$ on each occurrence, independently is hydrogen, $(C_1-C_3)$alkyl, hydroxy$(C_1-C_3)$alkyl, $(C_1-C_3)$alkoxy, cyano, halogen, aryl, or aryl-O—;
$R^c$ is hydrogen, or $(C_1-C_5)$alkyl optionally substituted by one or more same or different substituent(s) selected from the group of hydroxyl, $(C_1-C_3)$alkoxy, halogen, and thio; and
b is 0, 1, 2, 3, or 4;
or a pharmaceutically acceptable salt, solvate, hydrate, clathrate, polymorph, stereoisomer, enantiomer, or combination thereof.

In one embodiment, the compound is a compound of Formula (IIa):

Formula (IIa)

wherein each of E and G is absent, $(C_1-C_3)$alkylene, or $(C_2-C_3)$alkenylene, and both of E and G cannot be absent at the same time; and all other variables herein are as those defined for Formula (IA).

In a particular embodiment, the compound is a compound of Formula (III-A):

Formula (III-A)

In another embodiment, the compound is a compound of Formula (III-B):

Formula (III-B)

wherein ----- stands for a single bond or a double bond.

In still another embodiment, the compound is a compound of Formula (III-C)

Formula (III-C)

In yet another embodiment, the compound is a compound of Formula (III-D):

Formula (III-D)

wherein W is O or S, and -----, independently, stands for a single bond or a double bond.

In a certain embodiment, the compound is a compound of Formula (III-E):

Formula (III-E)

wherein

-----, independently, stands for a single bond or a double bond;

$R^c$ is hydrogen, or $(C_1-C_5)$alkyl optionally substituted by one or more same or different substituent(s) selected from the group of hydroxyl, $(C_1-C_3)$alkoxy, and halogen;

$R^1$, $R^2$, $R^3$, $R^a$, b and n are those defined in Formula (IA).

Certain exemplified compounds of the invention include, for example, compounds as follows:

(1S,5R,E)-4-(2,4-dimethoxybenzylidene)-3-(pyridin-3-yl)-2-azabicyclo[3.2.1]oct-2-ene ("3-(DMXB)-4(R),6(S)-EA");

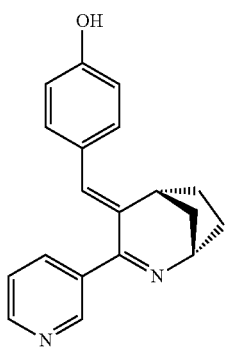 [SMILES: Oc1ccc(/C=C2/C(c3cccnc3)=N[C@H]3CC[C@@H]2C3)cc1]

4-((E)-((1S,5R)-3-(pyridin-3-yl)-2-azabicyclo[3.2.1]oct-2-en-4-ylidene)methyl)phenol ("3-(4OHB)-4(R),6(S)-EA");

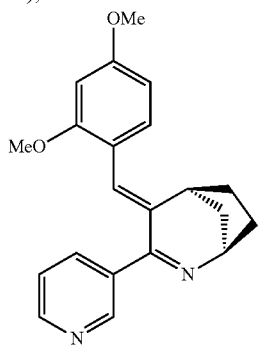

(1R,5S,E)-4-(2,4-dimethoxybenzylidene)-3-(pyridin-3-yl)-2-azabicyclo[3.2.1]oct-2-ene ("3-(DMXB)-4(S),6(R)-EA"); and

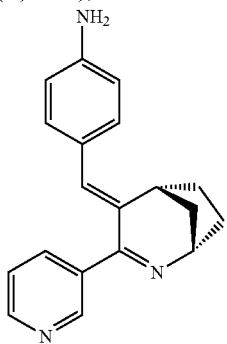

3-(4-Aminobenzylidene)-4(R),6(S)-ethylene-anabaseine ("3-(4AminoB)-4(R),6(S)-EA").

The invention also provides a compound of Formula (IIb):

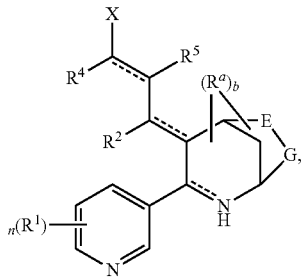

Formula (IIb)

wherein all the variables for Formula (IIb) are the same as those defined in Formula (IA).

The invention further provides a compound of Formula (IIc):

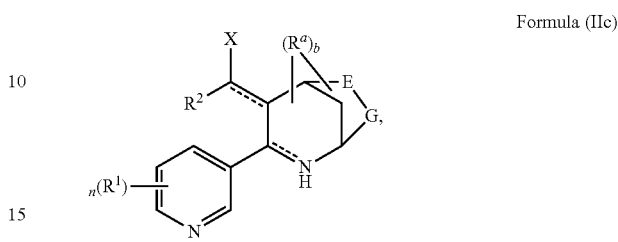

Formula (IIc)

wherein all the variables for Formula (IIb) are the same as those defined in Formula (IA).

Certain embodiments of the invention include, for example, a compound of Formula (i), (ii), (iii), or (iv):

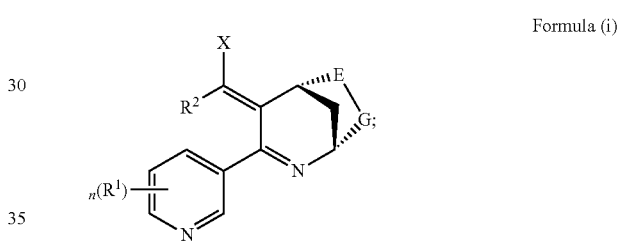

Formula (i)

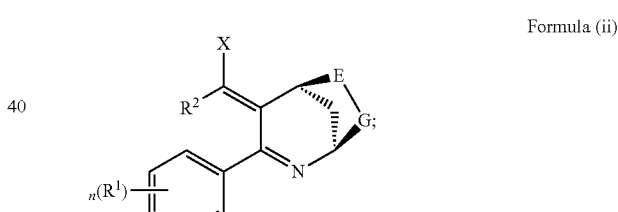

Formula (ii)

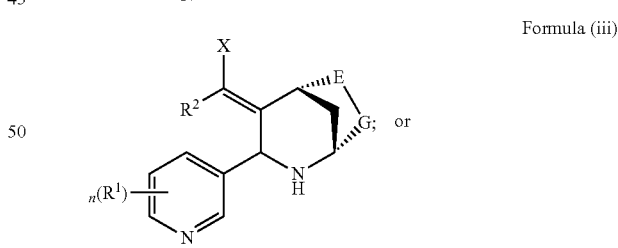

Formula (iii)

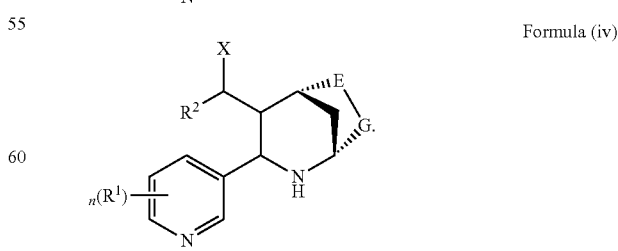

Formula (iv)

In a separate embodiment, the invention relates to a compound of Formula (IB):

Formula (IB)

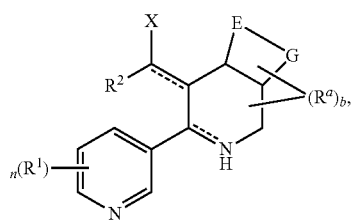

wherein all the variables for Formula (IB) are the same as those defined in Formula (I).

Other embodiments of the invention provide a compound of Formula (v), (vi), (vii) or (viii) as follows:

Formula (v)

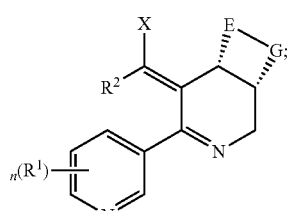

Formula (vi)

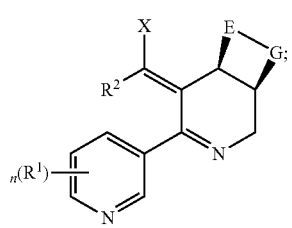

Formula (vii)

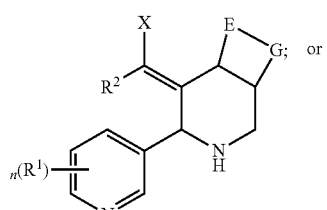

Formula (viii)

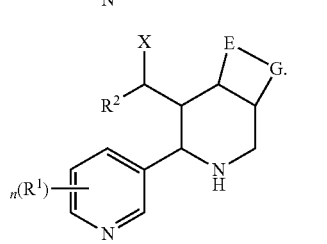

Further, the invention provides a compound of Formula (IC):

Formula (IC)

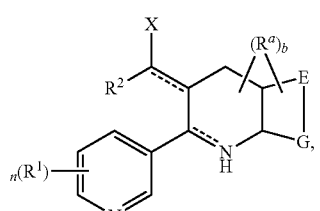

wherein all the variables for Formula (IC) are the same as those defined in Formula (I).

In certain embodiments, the compound is a compound of Formula (ix), (x), (xi), or (xii):

Formula (ix)

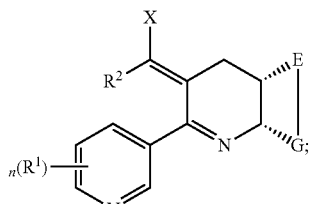

Formula (x)

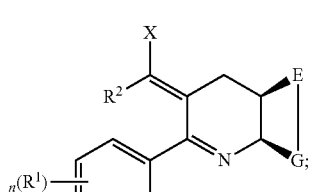

Formula (xi)

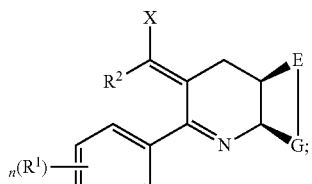

or

Formula (xii)

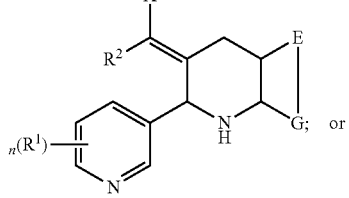

The invention also provides a compound of Formula (IV) as follows:

(IV)

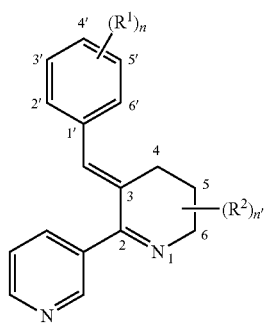

wherein
n is 1, 2, 3, 4, or 5;
n' is 1, 2, or 3;
$R^1$ is, independently, amino, $C_1$-$C_3$ alkyl, or $C_1$-$C_3$ alkoxy;
$R^2$ is, independently, $C_1$-$C_3$ alkyl; and at least one $R^2$ is present at position 4, 5, or 6; provided that when n is 2 and $R^1$ are both methoxy, n' is 2;

or a pharmaceutically acceptable salt, solvate, hydrate, clathrate, polymorph, stereoisomer, enantiomer, or combination thereof.

In a certain embodiment, the compound of the invention is a α7 nicotinic acetylcholine receptor agonist. In another embodiment, the compound of the invention is a α7 nicotinic acetylcholine receptor antagonist.

In one embodiment, a compound of the invention selectively binds to a α7 nicotinic acetylcholine receptor relative to a α4β2 nicotinic acetylcholine receptor. Another embodiment provides that a compound of the invention selectively binds to a α4β2 nicotinic acetylcholine receptor relative to a α7 nicotinic acetylcholine receptor.

One embodiment of the invention provides that the compound selectively activates a α7 nicotinic acetylcholine receptor. Another embodiment relates to a compound which selectively inhibits a α7 nicotinic acetylcholine receptor.

In another aspect, the invention provides a method for treating or preventing a nervous system disease or disorder in a subject identified as in need thereof. The nervous system diseases or disorders include, for example, dementia, schizophrenia, Alzheimer's disease, Parkinson's disease, drug dependence, and substance addiction. The method includes administering to a subject in need thereof an effective amount of a compound of the invention, which thereby prevents or treats the disease or disorder in the subject.

In one embodiment, the subject in need thereof is administered with an effective amount of a compound of Formula (III-A). In another embodiment, the subject in need thereof is administered with an effective amount of a compound of Formula (IV).

In certain embodiments, the subject in need thereof is administered with an effective amount of a compound, such as, one or more of (1S,5R,E)-4-(2,4-dimethoxybenzylidene)-3-(pyridin-3-yl)-2-azabicyclo[3.2.1]oct-2-ene ("3-(DMXB)-4(R),6(S)-EA"), 3-(4-Aminobenzylidene)-4(R),6(S)-ethylene-anabaseine ("3-(4AminoB)-4(R),6(S)-EA"), dl-3-(4-Hydroxybenzylidene)-4,6-ethyleneanabaseine, 3-(Arylidene)-4,6-ethylene-anabaseines, dl-3-(2,4-Dimethoxybenzylidene)-4,6-ethyleneanabaseine, 3-(4-Hydroxy-3-methoxycinnamylidene)-4(R),6(S)-ethyleneanabaseine, 3-(5-Acetoxyfurfurylidene)-4(R),6(S)-ethyleneanabaseine, 3-(Benzo[b]thiophen-2-ylidene)-4(R),6(S)-ethyleneanabaseine.

As another aspect, the invention relates to a method for the treatment or prevention of a disease or disorder in a subject in need thereof, wherein the disease or disorder is associated with α7 nicotinic acetylcholine receptor activity. Such diseases or disorders include, for example, inflammation and cancer. The method includes administering to a subject in need thereof an effective amount of a compound of the invention, which thereby prevents or treats the disease or disorder in the subject.

One embodiment provides that the subject is a mammal. Another embodiment provides that the subject is a human patient.

The invention further provides pharmaceutical compositions for the prevention or treatment of a disease or disorder above delineated. The compositions include a therapeutically effective amount of a compound of the invention and a pharmaceutically acceptable excipient.

The invention also provides kits for the prevention or treatment of a disease or disorder above delineated. The kits include a therapeutically effective amount of a compound of the invention and instructions for use thereof.

A separate aspect of the invention provides a method of selectively stimulating a α7 nicotinic receptor in a cell. The method comprises contacting the cell with an effective amount of a compound of the invention. In one embodiment, the compound is a compound of Formula (III-A). In another embodiment, the compound is a compound of Formula (IV)

The invention also provides a method of selectively inhibiting a α7 nicotinic receptor in a cell. The method comprises contacting the cell with an effective amount of a compound of the invention.

BRIEF DESCRIPTION OF THE DRAWINGS

FIG. 1 depicts the chemical structure of 3-(4-Hydroxy-3-methoxycinnamylidene)-4(R),6(S)-ethyleneanabaseine.

FIG. 2 depicts the chemical structure of 3-(Benzo[b]thiphen-2-ylidene)-4(R),6(S)-ethyleneanabaseine.

FIG. 3 depicts the chemical structure of 3-(5-Acetoxyfurfurylidene)-4(R),6(S)-ethyleneanabaseine.

FIG. 4 depicts the chemical structure of (1S,5R,E)-4-(2,4-dimethoxybenzylidene)-3-(pyridin-3-yl)-2-azabicyclo [3.2.1]oct-2-ene ("3-(DMXB)-4(R), 6(S)-EA").

FIG. 5 depicts the chemical structure of dl-3-(4-Hydroxybenzylidene)-4,6-ethyleneanabaseine

DETAILED DESCRIPTION OF THE INVENTION

In one aspect, the invention features novel compounds as delineated herein and methods of using such compounds for the treatment or prevention of a disease, disorder, or condition (e.g., a nervous system disease or disorder, lung cancer, wound healing, and inflammation) in a subject identified as in need thereof. In another aspect, the invention provides compounds and methods thereof for the treatment or prevention of a disease, disorder, or condition associated with α7 nicotinic acetylcholine receptor activity (e.g., treated by arylidene-anabaseine drugs selectively targeting α7 or α4β2 nicotinic acetylcholine receptors).

The invention is based, in part, on the discovery of novel ligands that selectively bind to α7 nAChR ligands; these include agonists (including partial agonists and full agonists) and antagonists. In another aspect, the invention is also based, in part, on the discovery of novel ligands that selectively bind to α4β2 nAChRs and can be either agonists or antagonists.

The present inventors have previously found that addition of an arylidene substituent at the 3-position of the tetrahydropyridyl ring of anabaseine creates compounds that selectively stimulate the α7 subtype nAChR, a therapeutic target for nervous system diseases or disorders as schizophrenia, Alzheimer's disease, Parkinson's disease, drug dependence and substance addition (see, e.g., US 2009/0215705). Nevertheless, the present inventors also observed that the previously patented compounds, while selectively activating α7 nAChRs, also can bind to α4β2 nAChRs and inhibit their normal functioning.

The present inventors unexpectedly discovered that novel anabaseine-based compounds having a certain chiral bicyclic tetrahydropyridyl ring scaffold display excellent binding as well as agonist selectivity for α7 nAChRs. The anabaseine-based compounds having the other (opposite) chiral bicyclic tetrahydropyridyl ring, have much less α7 binding affinity but essentially unchanged α4β2 nAChR affinity, and thus display binding selectivity for α4β2 nAChRs.

Initially, the present inventors prepared racemic 3-(arylidene)-4,6-ethylene-anabaseines and separated their two possible chiral forms by chiral high-performance liquid chromatography (HPLC). Pharmacological assays showed that only one of the two chiral forms of the compound displayed high α7 receptor binding affinity with respect to α4β2 type nAChR binding affinity. The inventors then carried out an asymmetric synthesis to obtain the chiral form, 4(R),6(S)-ethylene-anabaseine, and showed that the 3-arylidene derivatives of 4(R),6(S)-ethylene-anabaseine display significant improvements in binding affinity and selectivity for the α7 nAChR. The 3-(2,4-dimethoxybenzylidene)-4(R),6(S)-ethylene-anabaseine elutes with the same retention time as the chiral form displaying highest binding affinity and potency that was separated by chiral HPLC. The 3-(2,4-dimethoxy-benzlidene)-4(R),6(S)-ethylene-anabaseine was found to possess significantly greater selectivity for α7 nAChRs compared to 3-(DMXB)-anabaseine, also called GTS-21 (see Table 1 provided infra).

It is expected that the anabaseine derivatives of the invention demonstrate an enhanced α7 stimulatory activity, which is not opposed by a concurrent α4β2 inhibitory effect. The novel anabaseine derivatives of the invention also are expected to display fewer adverse effects that might result from inhibition of other nAChRs, due to their significantly higher α7 nAChR binding affinity, which in turn results in significant reduced dose that is needed for administration to a patient.

The present invention involves, in part, synthesis of racemic and chiral forms of anabaseine-based compounds containing a bicyclic tetrahydropyridyl ring, and their various possible substituted analogs.

The invention also provides a number of targets that are useful for the development of highly specific drugs to treat or prevent a disorder or disease characterized by the methods delineated herein. In addition, the methods of the invention provide a facile means to identify therapies that are safe/effective for use in subjects.

DEFINITIONS

Before a further description of the present invention, and in order that the invention may be more readily understood, certain terms are first defined and collected here for convenience.

The term "administration" or "administering" includes routes of introducing a compound(s) to a subject to perform their intended function. Examples of routes of administration that can be used include injection (subcutaneous, intravenous, parenterally, intraperitoneally, intrathecal), oral, inhalation, rectal and transdermal. The pharmaceutical preparations are, of course, given by forms suitable for each administration route. For example, these preparations are administered in tablets or capsule form, by injection, inhalation, topical by lotion or ointment; and rectal by suppositories. Oral administration is preferred. The injection can be bolus or can be continuous infusion. Depending on the route of administration, the compound can be coated with or disposed in a selected material to protect it from natural conditions which may detrimentally affect its ability to perform its intended function.

The compound can be administered alone, or in conjunction with either another agent as described above (e.g. another therapeutic agent) or with a pharmaceutically-acceptable carrier, or both. The compound can be administered prior to the administration of the other agent, simultaneously with the agent, or after the administration of the agent. Furthermore, the compound can also be administered in a proform which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In certain embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer. Cycloalkyls as described herein may have from 3-10 carbon atoms in their ring structure. In certain instances, the cycloalkyls have 3, 4, 5, 6 or 7 carbons in the ring structure.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, specifically from one to six, and most specifically from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In one embodiment, the term "lower alkyl" includes a straight chain alkyl having 3 or fewer carbon atoms in its backbone, e.g., $C_1$-$C_3$ alkyl.

The term "alkoxy," as used herein, refers to an alkyl or a cycloalkyl group which is linked to another moiety though an oxygen atom. Alkoxy groups can be optionally substituted with one or more substituents.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "alkylene" as used herein refers to an alkanediyl functional group. In particular, an alkyl group has two sites for connecting to other moieties. Examples of alkylenes include, but not limited to, —$CH_2$—, —$CH_2CH_2$—, and —$CH_2CH_2CH_2$—.

The term "ameliorate" means to decrease, suppress, attenuate, diminish, arrest, or stabilize the development or progression of a disease.

The terms "α7 nicotinic acetylcholine receptor agonist," "α7 nicotinic agonist," and "α7 nicotinergic receptor agonist," and cognates thereof, refer to compounds that bind to the α7 nicotinic acetylcholine receptor (nAChR) and stimulate the α7 nicotinic receptor (e.g., provide a pharmacological effect, for example, stimulation of angiogenesis). The agonist effect of a compound may be determined using methods routine in the field, for example, by measuring electrophysiologically or radioisotopically the ion flux or change in intracellular calcium concentration as described herein. A "partial agonist" is a compound that stimulates the α7 receptor, but whose maximal response is less than that of acetylcholine when measured under the same conditions. A "full agonist" is a compound whose maximal response is the same or greater than that of acetylcholine when measured under the same conditions. Chronic administration of α7 nicotinic agonists can stimulate or upregulate the concentration of α7 nAChRs.

The term "alteration" refers to a change (increase or decrease) in a parameter as detected by standard art known methods, such as those described herein.

The term "aryl" refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "cancer" refers to a malignant tumor of potentially unlimited growth that expands locally by invasion and systemically by metastasis. Examples of cancers include, but are limited to,
bladder cancer, breast cancer, kidney cancer, leukemia, colon cancer, rectal cancer, endometrial cancer, melanoma, lung cancer, pancreatic cancer, and etc.

The term "chiral" refers to molecules which have the property of non-superimposability of the mirror image partner, while the term "achiral" refers to molecules which are superimposable on their mirror image partner.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. "Detect" refers to identifying the presence, absence or amount of the object to be detected.

By "disease" is meant any condition or disorder that damages or interferes with the normal function of a cell, tissue, or organ.

The term "diastereomers" refers to stereoisomers with two or more centers of dissymmetry and whose molecules are not mirror images of one another.

The term "effective amount" refers to the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

A therapeutically effective amount of a compound delineated herein (i.e., an effective dosage) may range from about 0.1 µg to 20 milligram per kilogram of body weight per day (mg/kg/day) (e.g., 0.1 µg/kg to 2 mg/kg, 0.3-3 µg/kg, 0.18-0.54 mg/kg). In other embodiments, the amount varies from about 0.1 mg/kg/day to about 100 mg/kg/day. In still other embodiments, the amount varies from about 0.001 µg to about 100 µg/kg (e.g., of body weight). One of skill in the art can readily extrapolate from dosages shown to be effective in in vivo testing to dosages that are likely to be effective in humans. In one embodiment, about 0.1-200 mg/kg/day a compound of the invention (e.g., any of compound Nos. 2, 4, 6, 8, 21, 25, 28, 48 and 30) is administered to a mouse, preferably 1-100 mg/kg, more preferably 5-50 mg/kg. In another embodiment, a dog receives 1-20 mg/kg of such compounds. In another embodiment, a human subject receives 0.1 µg/kg to 2 mg/kg of a compound of the invention (e.g., any of compounds 2, 4, 6, 8, 21, 25, 28, 48 and 30) per day. In yet another embodiment, 0.3-3 µg/kg of such compounds is administered to a human subject. In still another embodiment, 0.18-0.54 mg/kg total per day is administered to a human subject. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound delineated herein can include a single treatment or, preferably, can include a series of treatments. In one example, a subject is treated with a compound delineated herein in the range of between about 0.1 µg to 20 milligram per kilogram of body weight per day (mg/kg/day) (e.g., 0.1 µg/kg to 2 mg/kg, 0.3-3 µg/kg, 0.18-0.54 mg/kg). In other embodiments, the amount varies from about 0.1 mg/kg/day to about 100 mg/kg/day. In still other embodiments, the amount varies from about 0.001 µg to about 100 µg/kg (e.g., of body weight). If desired, the dosage is administered one time per day, two times per day, or one time per week. Treatment is carried out for between about 1 to 10 weeks, preferably between 2 to 8 weeks, more preferably between about 3 to 7 weeks, and even more preferably for about 4, 5, or 6 weeks. It will also be appreciated that the effective dosage of a compound delineated herein used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, with said heteroatoms selected from O, N, and S, and the remainder ring atoms being carbon. Heteroaryl groups may be optionally substituted with one or more substituents. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl. In one embodiment of the invention, heteroaryl refers to thienyl, furyl, pyridyl, or indolyl.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moieties include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom ($C^{12}$) would be one in which the carbon atom of the compound is replaced with the $C^{13}$ isotope.

The term "inflammation" as used herein refers to a way in which the body reacts to infection, irritation or other injury, the key feature being redness, warmth, swelling and pain. The inflammatory response directs one's immune system components to the site of injury or infection and is manifest by increased blood supply and vascular permeability which allows chemotactic peptides, neutrophils, and mononuclear cells to leave the intravascular compartment. Microorganisms are engulfed by phagocytic cells (e.g., neutrophils and macrophages) in an attempt to contain the infection in a small-tissue space. The response includes attraction of phagocytes in a chemotactic gradient of microbial products, movement of the phagocyte to the inflammatory site and contact with the organism, phagocytosis (ingestion) of the organism, development of an oxidative burst directed toward the organism, fusion of the phagosome and lysosome with degranulation of lysosomal contents, and death and degradation of the organism. Staphylococci, gram-negative organisms, and fungi are the usual pathogens responsible for these infections (see definitions from MediciNet.com). Macrophages secrete a number of cytokine proteins that, when bloodborne, cause a more generalized or systemic inflammation (sepsis). Sepsis may develop rapidly and is a life threatening disorder in need of new drug therapies.

The term "modulate" refers to increases or decreases in a parameter in response to exposure to a compound of the invention.

The term "obtaining" as in "obtaining compound" is intended to include purchasing, synthesizing or otherwise acquiring the compound.

The term "optical isomers" as used herein includes molecules, also known as chiral molecules, are exact non-superimposable mirror images of one another.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "polymorph" as used herein, refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing.

The term "prodrug" includes inactive compounds with moieties that can be metabolized in vivo. (or which spontaneously are transformed within the body as a result of their chemical instability) into an active drug. Generally, prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino loweralkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Certain prodrug moieties are, for example, propionoic acid esters and acyl esters. Prodrugs which are converted to active forms through other mechanisms in vivo are also included.

Furthermore, the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. Both configurations, cis/trans and/or Z/E are encompassed by the compounds of the invention.

With respect to the nomenclature of a chiral center, the terms "S" and "R" configuration and "d" and "l" configuration are as defined by the IUPAC Recommendations. As to the use of the terms, diastereomer, racemate, epimer and enantiomer, these will be used in their normal context to describe the stereochemistry of preparations.

By "reference" is meant a standard or control condition.

The term "subject" includes organisms which are capable of suffering from a disease or disorder described herein or who could otherwise benefit from the administration of a compound of the invention, such as human and non-human animals. Preferred human animals include human patients suffering from or prone to suffering from a disease or disorder, as described herein. The term "non-human animals" of the invention includes all vertebrates, e.g., mammals, e.g., rodents, e.g., mice, and non-mammals, such as, non-human primates, also sheep, dog, cow, chickens, amphibians, and reptiles.

The phrases "systemic administration," "administered systemically", "peripheral administration" and "administered peripherally" as used herein mean the administration of a compound(s), drug or other material, such that it enters the patient's system and, thus, is subject to metabolism and other like processes, for example, subcutaneous administration.

As used herein, the term "tautomers" refers to isomers of organic molecules that readily interconvert by tautomerization, in which a hydrogen atom or proton migrates in the reaction, accompanied in some occasions by a switch of a single bond and an adjacent double bond.

The structures of the compounds of the invention may include asymmetric carbon atoms. Accordingly, the isomers arising from such asymmetry (e.g., all enantiomers and diastereomers) are included within the scope of this invention, unless indicated otherwise.

Such isomers can be obtained in substantially pure form by classical separation techniques and/or by stereochemically controlled synthesis.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases, such as brucine, quinine, ephedrine, strychnine, and the like. Alternatively, diastereomeric esters can be formed with enantiomerically pure chiral alcohols, such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

Compounds of the Invention

Novel compounds of the invention specifically exclude compounds of the prior art, including those disclosed and/or claimed in US 2009/0215705. Accordingly, the invention contemplates one or more subgenuses of compounds of Formula (I) described herein resulting from the exclusion of one of one or more compounds of the prior art, including those disclosed and/or claimed in US 2009/0215705.

In one aspect, the invention provides a compound of Formula (I):

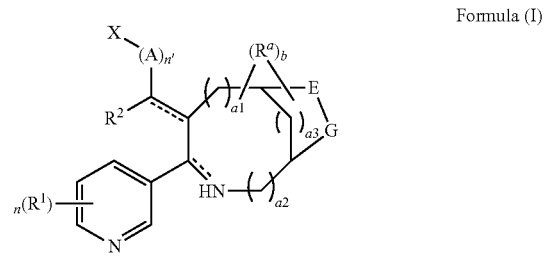

Formula (I)

wherein

------, independently, stands for a single bond or a double bond;

$R^1$, on each occurrence, independently is $(C_1-C_3)$alkyl, hydroxy$(C_1-C_3)$alkyl, $(C_1-C_3)$alkoxy, cyano, halogen, aryl-O—, aryl, or a 5- to 6-membered heteroaryl; or two $R^1$ groups, together with the bonds they are attached to, form a 5 to 8 membered cyclic ring;

n is 0, 1, 2, 3, or 4;

Each of a1, a2, and a3 is 0 or 1, wherein two of a1, a2, and a3 are 0, and the other is 1;

$R^2$ is hydrogen, $(C_1-C_3)$alkyl, hydroxy$(C_1-C_3)$alkyl, or $(C_1-C_3)$alkoxy;

E and G, each independently, are absent, -hetero$(C_0-C_3)$alkyl-, $(C_1-C_3)$alkylene, or $(C_2-C_3)$alkenylene, wherein E and G cannot be both absent at the same time;

A is a bond or

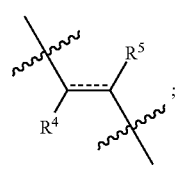

n' is 0, 1, or 2;

$R^4$ and $R^5$, on each occurrence, independently are hydrogen, $(C_1-C_3)$alkyl, hydroxy$(C_1-C_3)$alkyl, or $(C_1-C_3)$alkoxy;

X is aryl or heteroaryl, wherein said aryl and said heteroaryl are optionally substituted by one to five $R^3$ groups and/or one $R^c$ group;

$R^3$, on each occurrence, independently is hydrogen, halogen, $(C_1-C_3)$alkyl-C(O)O—, $(C_1-C_3)$alkyl-C(O)—, $(C_1-C_3)$alkyl-C(O)N($R^6$), N($R^6$)$_2$—, $(R^6)_2$NC(O)—, $(R^6)_2$N($C_1-C_5$) alkoxy, $(R^6)_3$N$^\oplus$($C_1-C_5$) alkoxy, hydroxyl, cyano, a sugar moiety or derivative thereof, $(C_1-C_3)$alkoxy optionally substituted by one or more same or different halogen or thio groups, or $(C_1-C_3)$alkyl optionally substituted by one or more same or different halogen or hydroxyl groups;

$R^6$, on each occurrence, independently is hydrogen, $(C_1-C_3)$alkyl, hydroxy$(C_1-C_3)$alkyl, or $(C_1-C_3)$alkoxy;

$R^a$ on each occurrence, independently is hydrogen, $(C_1-C_3)$alkyl, hydroxy$(C_1-C_3)$alkyl, $(C_1-C_3)$alkoxy, cyano, halogen, aryl, or aryl-O—;

$R^c$ is hydrogen, $(C_1-C_5)$alkoxy, or $(C_1-C_5)$alkyl, wherein said $(C_1-C_5)$alkoxy and said $(C_1-C_5)$alkyl are optionally substituted by one or more same or different substituents selected from the group of hydroxyl, $(C_1-C_3)$alkoxy, halogen, and thio; and b is 0, 1, 2, 3, or 4;

or a pharmaceutically acceptable salt, solvate, hydrate, clathrate, polymorph, stereoisomer, enantiomer, or combination thereof.

In one embodiment, the compound is a compound of Formula (IA)

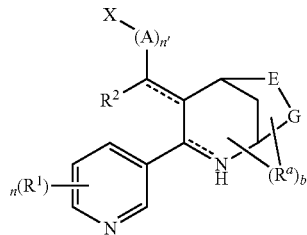

Formula (IA)

wherein

------, independently, stands for a single bond or a double bond;

$R^1$, on each occurrence, independently is $(C_1-C_3)$alkyl, hydroxy$(C_1-C_3)$alkyl, $(C_1-C_3)$alkoxy, cyano, halogen, aryl-O—, aryl, or a 5- to 6-membered heteroaryl; or two $R^1$ groups, together with the bonds they are attached to, form a 5 to 8 membered cyclic ring;

n is 0, 1, 2, 3, or 4;

$R^2$ is hydrogen, $(C_1-C_3)$alkyl, hydroxy$(C_1-C_3)$alkyl, or $(C_1-C_3)$alkoxy;

E and G, each independently, are absent, -hetero($C_0-C_3$)alkyl-, $(C_1-C_3)$alkylene, or $(C_2-C_3)$alkenylene, wherein E and G cannot be both absent at the same time;

A is a bond or

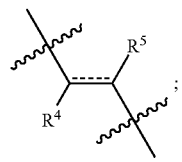

n' is 0 or 1;

$R^4$ and $R^5$, on each occurrence, independently are hydrogen, $(C_1-C_3)$alkyl, hydroxy$(C_1-C_3)$alkyl, or $(C_1-C_3)$alkoxy;

X is aryl or heteroaryl, wherein said aryl and said heteroaryl are optionally substituted by one to five $R^3$ groups and/or one $R^c$ group;

$R^3$, on each occurrence, independently is hydrogen, halogen, $(C_1-C_3)$alkyl-C(O)O—, $(C_1-C_3)$alkyl-C(O)N($R^6$), N($R^6$)$_2$—, $(R^6)_2$NC(O)—, $(R^6)_2$N($C_1-C_5$)alkoxy, $(R^6)_3$N($C_1-C_5$) alkoxy, hydroxyl, a sugar moiety or derivative thereof, $(C_1-C_3)$alkoxy optionally substituted by one or more same or different halogen or thio groups, or $(C_1-C_3)$alkyl optionally substituted by one or more same or different halogen or hydroxyl groups; and $R^6$, on each occurrence, independently is hydrogen, $(C_1-C_3)$alkyl, hydroxy$(C_1-C_3)$alkyl, or $(C_1-C_3)$alkoxy;

$R^a$ on each occurrence, independently is hydrogen, $(C_1-C_3)$alkyl, hydroxy$(C_1-C_3)$alkyl, $(C_1-C_3)$alkoxy, cyano, halogen, aryl, or aryl-O—;

$R^c$ is hydrogen, or $(C_1-C_5)$alkyl optionally substituted by one or more same or different substituent(s) selected from the group of hydroxyl, $(C_1-C_3)$alkoxy, halogen, and thio; and b is 0, 1, 2, 3, or 4;

or a pharmaceutically acceptable salt, solvate, hydrate, clathrate, polymorph, stereoisomer, enantiomer, or combination thereof.

One embodiment provides that each of E and G is absent or $(C_1-C_3)$alkylene, wherein E and G cannot be both absent at the same time.

In one embodiment, the invention provides a compound of Formula (IIa):

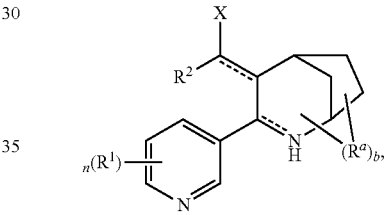

Formula (IIa)

wherein $R^1$, $R^2$, $R^a$, X, b, n are as delineated above in Formula (IA).

In one embodiment, X is an aryl group, which is optionally substituted by one to five $R^3$ groups. In a separate embodiment, X is an optionally-substituted heteroaryl group. In a certain embodiment, b is 0.

One embodiment of the invention provides a compound of Formula (III-A)

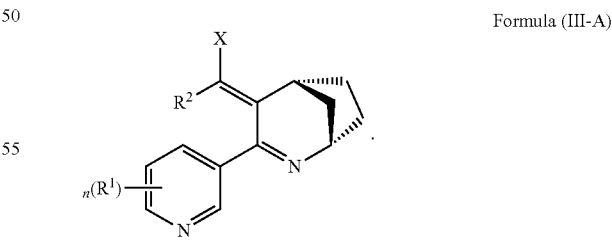

Formula (III-A)

X in Formula (III-A), for example, is an aryl group that is optionally substituted by one or two $R^3$ groups. In one embodiment, X is a phenyl group substituted by one or two $R^3$ groups, and $R^2$ is hydrogen. In a certain embodiment, n is 0. $R^3$ is, for example, amino, $(C_1-C_3)$alkoxy or hydroxyl.

Exemplified compounds of Formula (III-A) include, such as,

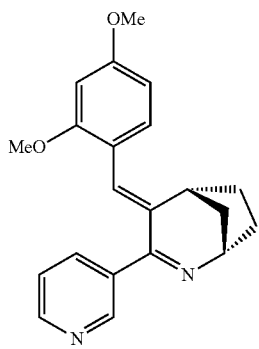 [SMILES: COc1ccc(/C=C2/C(c3cccnc3)=N[C@H]3CC[C@@H]2C3)c(OC)c1]

(1S,5R,E)-4-(2,4-dimethoxybenzylidene)-3-(pyridin-3-yl-2-azabicyclo[3.2.1]oct-2-ene ("3-(DMXB)-4(R),6(S)-EA");

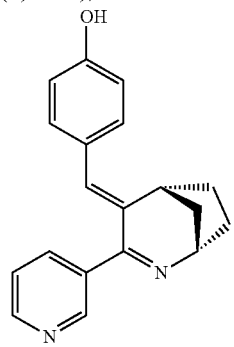

4-((E)-((1S,5R)-3-(pyridin-3-yl)-2-azabicyclo[3.2.1]oct-2-en-4-ylidene)methyl)phenol ("3-(4OHB)-4(R),6(S)-EA"); and

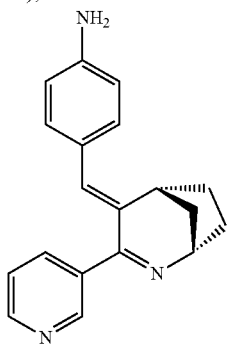

3-(4-Aminobenzylidene)-4(R),6(S)-ethylene-anabaseine ("3-(4AminoB)-4(R),6(S)-EA").

In another embodiment, the invention provides a compound of Formula (III-B)

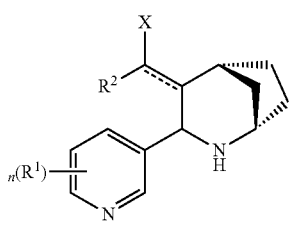

Formula (III-B)

wherein ----- stands for a single bond or a double bond.

Another embodiment provides a compound of Formula (III-C)

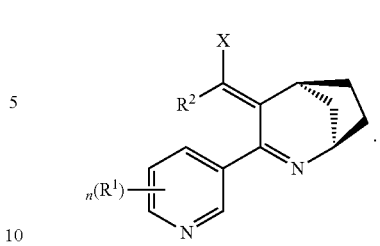

Formula (III-C)

X in Formula (III-C) can be, for example, an aryl group which is optionally substituted by one or two $R^3$ groups (such as, a phenyl group substituted by two ($C_1$-$C_3$)alkoxy groups). In one embodiment, n is 0. In another embodiment, $R^2$ is hydrogen. Exemplified compounds include, for example,

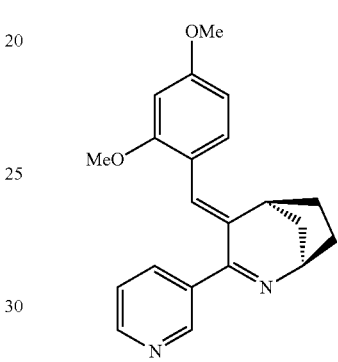

(1R,5S,E)-4-(2,4-dimethoxybenzylidene)-3-(pyridin-3-yl)-2-azabicyclo[3.2.1]oct-2-ene ("3-(DMXB)-4(S),6(R)-EA").

In a separate embodiment, the invention provides a compound of Formula (III-D):

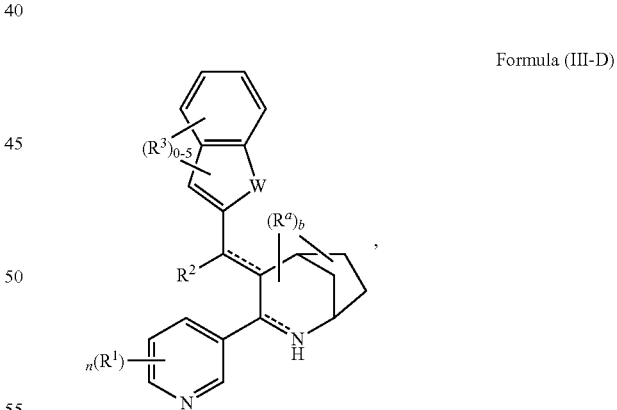

Formula (III-D)

wherein W is O or S, and -----, independently, stands for a single bond or a double bond. In one embodiment, b is 0. In another embodiment, $R^2$ is H. Certain embodiments provide that $R^3$, on each occurrence, independently is hydroxyl, alkyl, alkylamino, dialkylamino, or alkoxy.

In still another embodiment, the invention provides a compound of Formula (III-E):

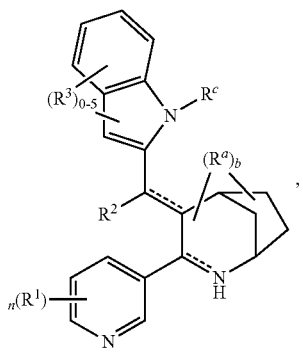
Formula (III-E)

wherein

------, independently, stands for a single bond or a double bond;

$R^c$ is hydrogen, or $(C_1-C_5)$alkyl optionally substituted by one or more same or different substituent(s) selected from the group of hydroxyl, $(C_1-C_3)$alkoxy, and halogen; and $R^1$, $R^2$, $R^3$, $R^a$, b, and n are those delineated for Formula (IA).

In yet another embodiment, X is aryl substituted by one to five $R^3$ groups, with at least one $R^3$ group is a sugar moiety or derivative thereof.

The compounds of formula (IA) also include a compound of Formula (IIb) or Formula (IIc) as follows:

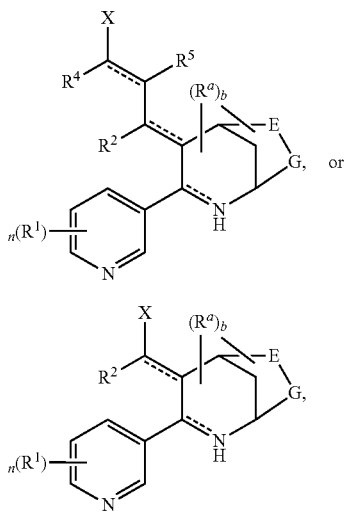
Formula (IIb)

Formula (IIc)

wherein ------, $R^1$, $R^2$, $R^4$, $R^5$, $R^a$, E, G, X, n, and b are those defined for Formula (IA). In one embodiment, X is an optionally substituted aryl. In another embodiment, b is 0. In a separate embodiment, one of E and G is absent or $(C_1-C_3)$ alkylene, the other is -hetero$(C_0-C_3)$alkyl.

In one embodiment, the compound of Formula (IIc) comprises, for example, a compound of Formula (i), (ii), (iii) or (iv):

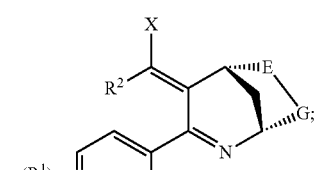
Formula (i)

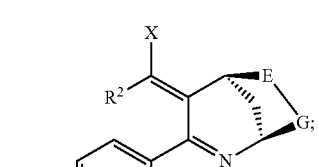
Formula (ii)

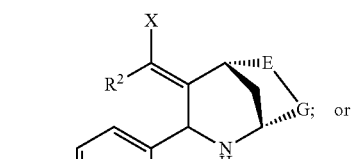
Formula (iii); or

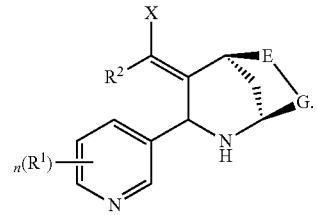
Formula (iv)

In another embodiment of compounds of Formula (I), the compound is a compound of Formula (IB):

Formula (IB)

wherein ------, $R^1$, $R^2$, $R^a$, E, G, X, n, and b are those as defined in Formula (I).

One embodiment provides that one of E and G is absent, and the other is —$CH_2$— or a heteroatom. Another embodiment provides that one of E and G is $(C_1-C_3)$alkylene or $(C_2-C_3)$alkenylene, and the other is hetero$(C_0-C_3)$alkyl. Examples include, such as, one of E and G is selected from the group of —$CH_2$—, —$CH_2$—$CH_2$—, —CH=CH—, —CH=CH—$CH_2$—, and —$CH_2$—$CH_2$—$CH_2$—, and the other is a heteroatom or -Het-$CH_2$—.

Certain embodiments of Formula (IB) provide a compound of Formula (v), (vi), (vii),

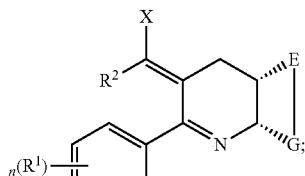

Formula (v)

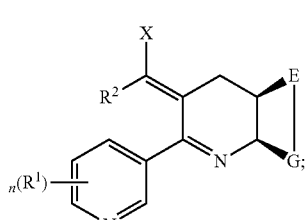

Formula (vi)

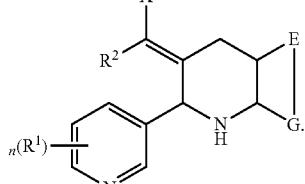

Formula (vii); or

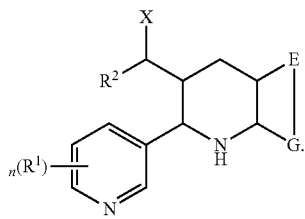

Formula (viii)

In still another embodiment of compounds of Formula (I), the compound is a compound of Formula (IC):

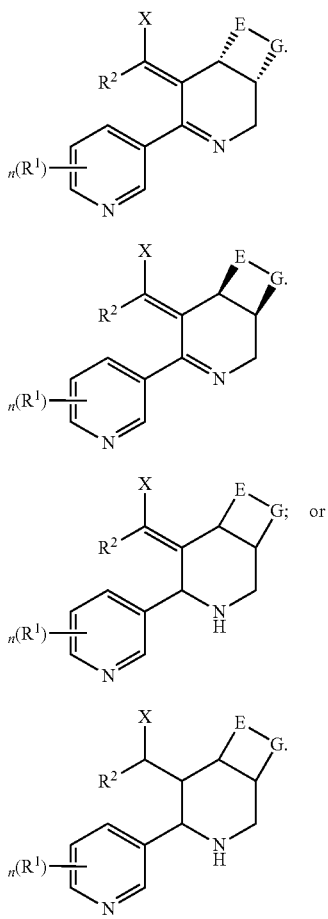

Formula (IC)

wherein -----, $R^1$, $R^2$, $R^a$, E, G, X, n, and b are those defined in Formula (I).

A certain embodiment provides that one of E and G is absent, and the other is —CH$_2$— or a heteroatom. Another embodiment provides that one of E and G is (C$_1$-C$_3$)alkylene, and the other is hetero(C$_0$-C$_3$)alkyl. Examples include, such as, one of E and G is selected from the group of —CH$_2$—, —CH$_2$—CH$_2$—, and —CH$_2$—CH$_2$—CH$_2$—, and the other is a heteroatom or -Het-CH$_2$—.

Certain embodiments of Formula (IC) provide a compound of Formula (ix), (x), (xi), or (xii):

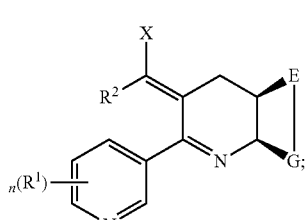

Formula (ix)

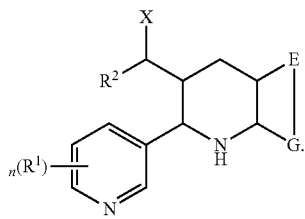

Formula (x)

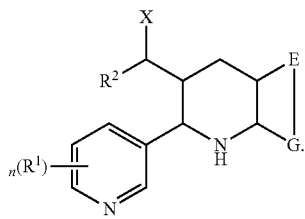

Formula (xi)

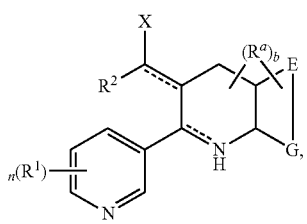

Formula (xii)

Further, the invention also provides a compound of Formula (IV), or a pharmaceutically acceptable salt, solvate, hydrate, clathrate, polymorph, stereoisomer, enantiomer, or combination thereof:

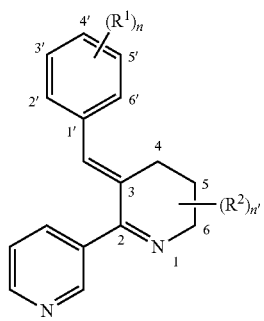

(IV)

wherein
n is 1, 2, 3, 4, or 5;
n' is 1, 2, or 3;
$R^1$ is, independently, amino, C$_1$-C$_3$ alkyl, or C$_1$-C$_3$ alkoxy;
$R^2$ is, independently, C$_1$-C$_3$ alkyl; and at least one $R^2$ is present at position 4, 5, or 6; provided that when n is 2 and $R^1$ are both methoxy, n' is 2.

In one embodiment of Formula (IV), $R^1$ is, independently, amino or methoxy. In a separate embodiment, $R^2$ is, independently, $C_1$-$C_3$ alkyl (e.g., methyl). In one embodiment, n is 1 or 2. In another embodiment, n' is 1 or 2.

Exemplified compounds of Formula (IV) include, such as,

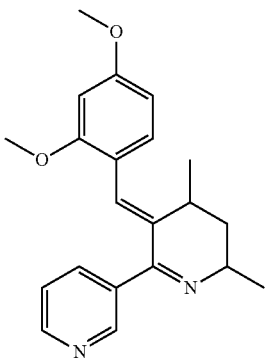

3-(2,4-Dimethoxybenzylidene)-dl-4,6-dimethyl-anabaseine; and

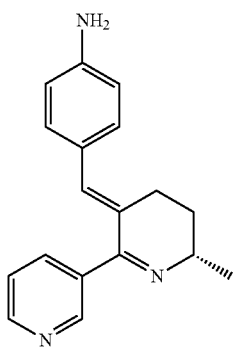 [SMILES: C[C@H]1CC/C(=C\c2ccc(N)cc2)C(c2cccnc2)=N1]

3-(4-Aminobenzylidene)-6(S)-methyl-anabaseine ("3-(4AminoB)-6(S)Me-A").

The invention also relates to a pharmaceutically acceptable salt, solvate, clathrate, hydrate, polymorph, prodrug, stereoisomer, or enantiomer thereof, of the compounds above discussed.

Certain embodiments provide that the compound of the invention is a α7 nicotinic acetylcholine receptor agonist. A separate embodiment provides that a compound of the invention is a α7 nicotinic acetylcholine receptor antagonist.

In one embodiment, a compound of the invention selectively binds to a α7 nicotinic acetylcholine receptor with higher affinity relative to a α4β2 nicotinic acetylcholine receptor. Yet in another embodiment, a compound of the invention selectively binds to a α4β2 nicotinic acetylcholine receptor with higher affinity relative to a α7 nicotinic acetylcholine receptor.

One embodiment of the invention relates to a compound which selectively activates a α7 nicotinic acetylcholine receptor. Another embodiment of the invention provides a compound, which selectively inhibits a α7 nicotinic acetylcholine receptor.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

In another aspect, the invention provides the use of a compound of any of the formulae herein, alone or together with one or more additional therapeutic agents in the manufacture of a medicament, either as a single composition or as separate dosage forms, for treatment or prevention in a subject of a disease, disorder or symptom set forth herein. Another aspect of the invention is a compound of the formulae herein for use in the treatment or prevention in a subject of a disease, disorder or symptom thereof delineated herein.

Methods of synthesizing compounds herein are within the means of chemists of ordinary skill in the art. Methods for optimizing reaction conditions, if necessary minimizing competing by-products, are known in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Uses of the Compounds of the Invention

The invention also provides methods for treating or preventing a nervous system disease or disorder in a subject identified as in need thereof. The method includes administering to the subject an effective amount of a compound of the invention. The nervous system disease or disorder, for example, is schizophrenia, Alzheimer's disease, Parkinson's disease, drug dependence, or substance addiction.

The invention also provides a method for the treatment or prevention of a disease or disorder associated with α7 nicotinic acetylcholine receptor activity (e.g., inflammation, cancer, or surgery-related disorders) in a subject in need thereof.

The method comprises administering to the subject an effective amount of a compound of the invention.

It is believed that certain compounds of the invention are ready for absorption through oral administration, and can easily pass into the brain. Thus, they have excellent drug-like properties.

In some embodiments, the subject is a mammal, including, but not limited to, bovine, equine, feline, rabbit, canine, rodent, or primate. In particular embodiments, the mammal is a primate. In certain embodiments, the primate is a human.

In certain embodiments, the subject has been identified as having one or more of the diseases or disorders described herein. Identification of the diseases or disorders as described herein by a skilled physician is routine in the art and may also be suspected by the individual. As for example, in proliferative retinopathies, when an individual notices to loss of vision or visual acuity (e.g., reduction in the field of vision, blurriness, etc.).

In some embodiments, the subject has been identified as susceptible to one or more of the diseases or disorders as described herein. The susceptibility of a subject may be based on any one or more of a number of risk factors and/or diagnostic approaches appreciated by the skilled artisan, including, but not limited to, genetic profiling, family history, medical history (e.g., appearance of related conditions (e.g., diabetes for diabetic ulcers, proliferative retinopathies, etc.), lifestyle or habits).

The terms, "pharmaceutically effective amount" or "therapeutically effective amount," and cognates of these terms, as used herein refer to an amount of a formulation sufficient to treat a specified condition (e.g., disease, disorder, etc.) or one or more of its symptoms and/or to prevent the occurrence of the condition. In reference to cancers, a pharmaceutically or therapeutically effective amount comprises an amount sufficient to, among other things, cause a tumor to shrink, or to decrease the growth rate of the tumor.

While certain compounds of the invention are agonists of the α7 nicotinic receptor, certain compounds are α7 nicotinic receptor antagonists. Determination of agonist/antagonist activity can be accomplished using techniques known to those of skill in the art, particularly in view of the teaching provided herein. The most direct method of determining whether a compound is a nicotinic agonist or antagonist is to measure the ion flux caused by activation of the nAChR ion channel as a result of exposure to that compound. A number of cell lines expressing a particular mammalian nAChR are available for such use. The ion flux or change in intracellular calcium concentration can be measured with radioisotopically labeled ions or in some cases by calcium ion imaging (nAChRs are permeable to calcium ions as well as sodium and potassium ions). Additionally, the net flux of all ions can be measured electrophysiologically, probably the customary method for assessing the functional properties of nAChR compounds. In the present application, the inventors transiently transfected messenger RNAs of the particular nAChR in frog (*Xenopus laevis*) oocytes, which readily express the nAChR subunits for which mRNA are injected over a period of several days. The response of a perfused oocyte to a rapid application of compound was measured with a standard two microelectrode voltage-clamp method where one intracellular electrode measures the internal potential relative to a large external electrode and the other intracellular microelectrode is used to pass a current needed to maintain the cell membrane potential at a predetermined intracellular voltage (usually −60 millivolts). When the nicotinic receptors are stimulated by an agonist, the inward current needed to clamp the membrane potential at −60 mV is recorded as a function of time and either the peak current or the integrated current over several hundred milliseconds is used as a measure of nAChR activation. Current responses were always measured relative to the response to a standard concentration of acetylcholine, usually 1,000 micromolar for the α7 receptor. Increasing concentrations were tested, using a minimum of three oocytes per concentration to construct a concentration-response curve. The concentration of compound required to produce 50% of the maximal normalized current that could be produced by that compound was measured by curve-fitting with a modified Hill equation. The $EC_{50}$ is an inverse measure of agonist potency: the lower the $EC_{50}$, the higher the potency. If a compound was not stimulatory, its ability to be an antagonist was measured by coapplying different concentrations with the standard ACh calibrating pulse. The median inhibitory concentration ($IC_{50}$) was thus measured. The lower the $IC_{50}$ concentration, the more potent the compound's inhibitory potency.

As will be understood by one of ordinary skilled in the art, the compounds described herein, when identified as agonists (including partial agonists and full agonists) or antagonists of the α7 nicotinic receptor can be used in the treatment and/or prevention of conditions (e.g., diseases or disorders) that are mediated by agonism or antagonism of the α7 nicotinic receptor, such as the conditions described herein. For example, antagonists can be used in the treatment of conditions where a reduction in angiogenesis is desirable (e.g., macular degeneration and related conditions (e.g., age-related macular degeneration and other conditions characterized by abnormal neovascularization of the retina and/or choroid, or proliferative retinopathies); cancer or other conditions related to abnormal proliferation, etc. Additional conditions amenable to treatment with α7 nicotinic receptor antagonists are known in the field and described, for example, in WO 03/068208, the disclosure of which is herein incorporated by reference in its entirety.

Similarly, compounds that are α7 nicotinic receptor agonists can be used in conditions where stimulation of α7 nicotinic receptor function is desired. For example, where stimulation of angiogenesis is indicated for therapeutic effect (e.g., wound healing, e.g., of diabetic ulcers, non-healing wounds, etc.) and where nicotinic receptor deficits have been implicated in neurodegenerative conditions and cognitive disorders (such as, e.g., AD and schizophrenia). Additional conditions amenable to treatment with α7 nicotinic receptor full agonists or partial agonists are known in the field and described, for example, in U.S. Pat. Nos. 6,417,205; 6,720,340, 5,977,144; 5,741,802; and U.S. Pat. App. Pub. No. 2005/004550, the disclosures of which are incorporated by reference in their entirety.

In certain embodiments, the pharmaceutically effective amount is sufficient to prevent the condition, as in being administered to an individual prophylactically.

The compounds and pharmaceutical formulations thereof and methods described herein may be used alone or in conjunction with (e.g., prior to, concurrently with, or after) other modes of treatment (e.g., adjunctive therapy with additional agents used to treat or prevent the condition being treated and/or administration of an additional treatment modality, or combinations thereof). For example, the compounds may be used in combination with one or more additional pharmaceutical agents (also referred to as therapeutic agents) as described herein and known to those of skill in the art and/or currently available as treatment modalities. As used herein, the term "additional treatment modality" refers to treatment of the conditions described herein without the use of a pharmaceutical agent (e.g., for proliferative retinopathies, one or more of thermal laser photocoagulation, photodynamic therapy, etc.; for cancer, one or more of surgery, radiation therapy, etc). Where combinations of pharmaceutical agent(s) and/or additional treatment modality(ies) are used, they may be, independently, administered prior to, concurrently with, or after administration of the compounds or pharmaceutical formulations thereof, as described herein.

The compounds or pharmaceutical formulations thereof described herein can be administered in conjunction with one or more of the pharmaceutical agents as described herein and, as known in the art, one or more additional agents to further reduce the occurrence and/or severity of side effects reactions and/or clinical manifestations thereof, or in conjunction with (e.g., prior to, concurrently with, or after) adjunctive therapies as described herein. The compounds or pharmaceutical formulations thereof as described herein may be administered before, concurrently with, or after the administration of one or more of the pharmaceutical agents described herein. The formulations thereof described herein may also be administered in conjunction with (e.g., prior to, concurrently with, or after) agents to alleviate the symptoms associated with either the condition or the treatment regimen.

The optimal combination of one or more of surgery and/or additional agents in conjunction with administration of the compounds or pharmaceutical formulations thereof described herein can be determined by an attending physician based on the individual and taking into consideration the various factors affecting the particular individual, including those described herein.

A separate aspect of the invention provides a method of selectively stimulating a α7 nicotinic receptor in a cell. The method comprises contacting the cell with an effective amount of a compound of the invention. In one embodiment, the compound is a compound of Formula (III-A). In another embodiment, the compound is a compound of Formula (IV).

The invention also provides a method of selectively inhibiting an α7 nicotinic receptor in a cell. The method comprises contacting the cell with an effective amount of a compound of the invention.

A separate aspect of the invention provides a method of selectively inhibiting a α4β2 nAChR in a cell. The method comprises contacting the cell with an effective amount of a compound of the invention. In one embodiment, the compound is a compound of Formula (III-A). In another embodiment, the compound is a compound of Formula (IV).

The invention also provides the use of one or more compounds, such as, 3-(2,4-Dimethoxybenzylidene)-4(S)-methyl-anabaseine ("3-(DMXB)-4(S)-Me-A"); 3-(2,4-Dimethoxybenzylidene-dl-5-methyl-anabaseine (racemic mixture of "3-(DMXB)-5(R)-Me-A" and "3-(DMXB)-5(S)-Me-A"); 3-(2,4-Dimethoxybenzylidene)-6(S)-methyl-anabaseine ("3-(DMXB)-6(S)-Me-A"); 3-(2,4-Dimethoxybenzylidene)-dl-4,6-dimethyl-anabaseine; and 3-(4-Aminobenzylidene)-6(S)-methyl-anabaseine ("3-(4AminoB)-6(S)Me-A") for purposes above delineated.

In a particular embodiment, the compound of the invention is (1S,5R,E)-4-(2,4-dimethoxybenzylidene)-3-(pyridin-3-yl)-2-azabicyclo[3.2.1]oct-2-ene ("3-(DMXB)-4(R),6(S)-EA") or 3-(4-Aminobenzylidene)-4(R),6(S)-ethylene-anabaseine ("3-(4AminoB)-4(R),6(S)-EA"), or a pharmaceutically acceptable salt, solvate, hydrate, clathrate, polymorph, stereoisomer, enantiomer, or combination thereof.

Conditions to be Treated

The invention is expected to be useful in a number of applications, particularly in treatment of diseases or disorders where it is advantageous to increase α7 nicotinic receptor activity. Loss of α7 receptors occurs in the progression of AD and there is deficient expression of this receptor subtype in schizophrenia. It has been shown that chronic administration of α7 agonists like 3-(2,4-dimethoxy benzylidene)-anabaseine (DMXBA) can lead to an increased expression of functional α7 receptors on cell surfaces. Thus, chronic administration of a α7-selective drug may have an even greater effect than before up-regulation in α7 number and responsiveness has occurred. An up-regulation in responsiveness is expected with the compounds of the invention, either alone or in combination, in appropriate pharmaceutically acceptable forms. Possible applications of these new α7 agonists and antagonists based on the anabaseine structure include therapeutic treatments for neurodegenerative, neurodevelopmental and addiction diseases involving nAChRs, as well as potential development as anti-proliferative, anti-inflammatory and wound-healing drugs acting systemically. In particular, it is shown that altering anabaseine compound polarity and ionization can permit drug application and localization to the peripheral (blood and interstitial fluid) compartments without significant entry into the central nervous system.

The nAChR population in the AD brain at death is greatly reduced relative to a normal aging brain. Neurodegeneration is most obvious in the neocortex and the hippocampus regions associated with higher mental functions. The two most abundant nAChR subtypes can be separately measured using the radiolabeled snake toxin alpha-bungarotoxin for the α7 subtype and radiolabeled (S)-nicotine or cytisine for the α4β2 nAChR subtype. Recent studies in AD brains showed that in the neocortex the major loss of binding sites with nicotine agonists is associated with a marked reduction in the α4β2 nAChRs and a much smaller reduction in α7 nAChRs. Using either in situ hybridization or monoclonal antibodies, there is a decrease in both the α4 (40%) and the α7 (17%) subunit protein expression in AD cortices compared to age-matched controls. Since there is less significant reduction in the α7 nAChR subtype in Alzheimer's disease patients, it is an attractive target for therapeutic drugs that can stimulate the function of the remaining receptors.

Harmful peptides such as $\beta$-amyloid$_{1-42}$ formed through the abnormal cleavage of amyloid precursor protein (APP) may be responsible for AD. APP is a transmembrane protein located on the surface of cells in many tissues and organs. The exact function of this protein is not known; however, it has been implicated in nerve cell growth and movement and as a gene switch. $\beta$-amyloid$_{1-40}$ is present in the brain and cerebrospinal fluid of normal subjects in picomolar concentrations. In AD patients, there is evidence of an elevated level of $\beta$-amyloid$_{1-42}$, which exhibits toxic effects on neurons. The $\beta$-amyloid$_{1-42}$ peptide may lose its helical shape and form fibrils with other proteins, making them less soluble. As these fibrils bind with other fibrils, amyloid plaques are ultimately formed that are found in high concentrations in persons with Alzheimer's disease. The neuronal degeneration associated with AD seems to be related to some as yet unidentified soluble or insolubilized form of $\beta$-amyloid.

Evidence for a more direct involvement of the α7 nAChR in Alzheimer's disease (AD) is the ability of $\beta$-amyloid$_{1-42}$ to bind to the α7 receptor, as suggested by the co-immunoprecipitation of $\beta$-Amyloid$_{1-42}$ with the α7 receptor in samples from postmortem AD hippocampus. Additionally, α7 antagonists and $\beta$-amyloid competitively bind to heterologously expressed α7 receptors. If the α7 receptor is a receptor for $\beta$-amyloid$_{1-42}$ neurotoxicity, selective α7 nAChR full agonists, partial agonists or antagonists which prevent β-amyloid from binding to this receptor may also inhibit the development of AD.

In addition to CNS applications, this invention is expected to provide therapeutic agents that selectively stimulate peripheral α7 receptors expressed on non-neuronal cells, such as, macrophages, vascular endothelium and bronchial epithelium, which are peripheral cells known to express functional α7 nAChRs. When macrophage α7 receptors are stimulated, the secretion of inflammatory cytokines such as TNF is inhibited. These cytokines are known to exacerbate an immune response when overproduced and not efficiently removed from the system. Stimulation of vascular endothelial cells, for example, is known to enhance angiogenesis. Similarly, stimulation of α7 nAChRs in vascular endothelium enhances the formation of new blood vessels (angiogenesis), an important process in wound healing. On the other hand, proliferation of certain small cell lung cancers expressing primarily α7 nAChRs can be stimulated by nicotinic agonists and possibly inhibited with certain nicotinic antagonists. Thus, besides being implicated as useful therapeutic targets for treating nervous system disorders such as AD and schizophrenia, α7 nAChRs on non-neuronal cells may also be therapeutic targets for treating other disease states involving inflammation, trauma, deficient or excessive angiogenesis, and abnormal proliferation (cancer).

An important aspect of the invention is the expectation of providing a variety of substituted 3-arylidene-anabaseines (containing a bicyclic tetrahydropyridine moiety) displaying a range of agonistic efficacies at alpha7 nicotinic receptors. Factors to be taken into consideration include disposition of the therapeutic target, whether CNS or peripheral within systemic circulation, or contained within an organ with unique access such as the lung; possible side effects of the alpha7 drug at sites other than the intended target as well as through the intended target; and the need for a highly selective agonist, in addition to the age, sex, and general health of the patient. For example, it may be advantageous to use an arylidene-3-arylidene-anabaseine (containing a bicyclic tetrahydropyridine moiety) compound that does not cross the blood brain barrier when systemic and other peripheral inflammations are being treated and the alpha7 receptors on macrophages are being targeted. In treating pulmonary inflammation, it may be preferable to utilize an anabaseine that does not readily pass into the systemic circulation after being administered through an inhaler directly into the pulmonary space.

It is expected that the compounds of the invention may also exhibit pharmacokinetic as well as pharmacodynamic properties that are distinctly superior to previously synthesized and tested compounds and which would not have been predicted. Addition of a chemical group to improve compound potency, efficacy and selectivity may also make the compound less readily metabolized by protecting otherwise reactive sites on the molecule. For example, benzylidene-anabaseines containing methoxy substituents on the arylidene ring are readily O-dealkylated by hepatic cytochrome P450 enzymes to hydroxy- and ultimately glucuronido-hydroxy metabolites. Replacement of these alkoxy groups with other substituents may improve potency, selectivity, bioavailability, and/or plasma half-life (a measure of how long the administered drug stays available for therapeutic effect). Thus, position of the substituents providing alpha7 selectivity may also improve the pharmacokinetic properties of the arylidene-anabaseine.

Thus, in some embodiments, are provided compounds of the invention that are useful in the treatment of conditions mediated by α7 nicotinic receptors. Conditions which may be treated with the compounds described herein (and pharmaceutical formulations thereof), include conditions in which the desired therapy includes the stimulation of the α7 nicotinic receptors (i.e., use of the compounds described herein which are α7 nicotinic receptor agonists) or the inhibition of the α7 nicotinic receptors (i.e., use of the compounds described herein which are α7 nicotinic receptor antagonists).

The activity and/or selectivity of the compounds described herein, including whether a particular compound is an agonist (including partial agonist or full agonist) or antagonist of the α7 nicotinic receptor can be determined using methods known to the skilled artisan, particularly in view of the teachings provided herein. Methods for the characterization of the compounds of the invention can also be found, for example, in U.S. Pat. Nos. 5,581,785; 5,741,802; 5,977,144; and 6,630,491, the disclosures of which are incorporated by reference in their entirety.

In certain embodiments, the compounds of the invention, which are α7 nicotinic receptor agonists, may be used in the treatment of conditions that are treatable by the stimulation of the α7 nicotinic receptor, including, for example, neurological conditions (e.g., AD, Parkinson's Disease; vascular dementia; age-related cognitive decline (AACD); mild cognitive impairment (MCI); AIDS-related dementia; schizophrenia; bipolar disorder; stimulant addiction (e.g., to cocaine, amphetamines, etc.); psychoses (e.g., manic psychoses, etc.); enhancing cognitive behavior (e.g., enhancing learning, memory retention, etc.); glutamate-induced toxicity toward cortical cells; inflammation (e.g., the stimulation of α7 receptors in peripheral macrophages, etc.); conditions treatable by the stimulation of angiogenesis (e.g., wound healing (e.g., diabetic ulcers, wounds in non-diabetics, etc.)) and other conditions known to be treatable by the stimulation of alpha7 nicotinic receptors (e.g., conditions as described in U.S. Pat. Nos. 5,581,785; 5,741,802; 5,977,144; and 6,630,491)).

In addition, agonism of the α7 nicotinic receptor has also been linked to treatment of the additional conditions, including, but not limited to, inflammatory bowel disease (including, but not limited to, ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotropic lateral sclerosis (ALS), cognitive dysfunction, tinnitus, hypertension, bulimia, anorexia, obesity, cardiac arrythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), Huntington's Chorea, tardive dyskinesia, hyperkinesia, dyslexia, multi-infarct dementia, age related cognitive decline, epilepsy, including petit mal absence epilepsy, senile dementia, attention deficit hyperactivity disorder (ADHD) and Tourette's Syndrome.

In certain embodiments, the condition to be treated is a neurodegenerative condition. For example, AD, Parkinson's Disease, vascular dementia, AACD, MCI, AIDS-related dementia, schizophrenia, bipolar disorder, stimulant addiction (e.g., to cocaine, amphetamines, etc.) psychoses (e.g., manic psychoses, etc.). In some embodiments, the condition to be treated is AD, Parkinson's Disease, or vascular dementia. In other embodiments, the condition is schizophrenia.

Inflammation is one of several mechanisms employed by the body to fight infections and in normal circumstances is deployed only for sufficient time to alleviate or eliminate the source of disease or foreign invader. Part of the immune response is activation of macrophages. These cells release cytokines such as tumor necrosis factor (TNF) that induce expression of molecules that enhance inflammation.

Unfortunately, the immune response is not always confined to the location where it is needed. This may lead to sepsis (e.g., when TNF and bacteria are recruited to fight infection and they enter the systemic blood circulation) or, the immune system may begin to attack the body it is intended to protect. Chronic inflammatory disorders such as Crohn's Disease, certain forms of arthritis and even heart disease are now thought to be precipitated by inflammation. Additionally, there are many diseases now thought to result from an autoimmune response, including systemic lupus erythematosus, autoimmune hemolytic anemia, membranous glomerulonephritis, autoimmune polyendocrinopathies, autoimmune thyroiditis, idiopathic thrombocytopenic purpura, Addison's disease, insulin-dependent diabetes mellitus, etc. Acute inflammation of specific organs may also be treated with the same alpha7 nAChR agonists.

Thus, in some embodiments, the compounds of the invention, which are $\alpha 7$ nicotinic receptor agonists, may be used in the treatment of conditions that include inflammation as a symptom or precursor. For example, in some embodiments the condition to be treated is an autoimmune condition. In particular embodiments, the condition is systemic lupus erythematosus, autoimmune hemolytic anemia, membranous glomerulonephritis, autoimmune polyendocrinopathies, autoimmune thyroiditis, idiopathic thrombocytopenic purpura, Addison's disease or insulin-dependent diabetes mellitus.

The compounds of the invention that are being developed as selective $\alpha 7$ nAChR drugs for treatment of inflammation and autoimmune diseases are agonists. The relation between $\alpha 7$ receptors on macrophages and cytokine secretion (TNF, IL-4, IL-6) has been determined from studies in which the vagus nerve was stimulated (to produce TNF) in $\alpha 7$-deficient mice, resulting in an exaggerated inflammatory response to an immunostimulatory lipopolysaccharide because $\alpha 7$ receptors on macrophages normally are stimulated by the vagally-released acetylcholine and this inhibits TNF secretion from the macrophages. The presence of $\alpha 7$ receptors on macrophages is therefore considered to make them an excellent target for controlling inflammation by employing these new compounds in cases where there is an excessive proliferation of macrophages in the peripheral system. Some compounds of the invention are targeted for use in treatment of peripheral system inflammation such as sepsis. The compounds selected would not cross the blood brain barrier and therefore would remain outside the central nervous system.

It is believed that $\alpha 7$ nicotinic receptor agonists may be useful in stimulating angiogenesis in wound healing and other conditions in which there is inadequate tissue perfusion. New tissue requires a robust blood supply in order to function efficiently and tissue lacking sufficient oxygenation may become necrotic. Development of new blood vessels is of prime importance in recovery of damaged heart tissue. The brain is the site of several types of insults, including stroke and vascular dementia and there is a decrease in number of microvessels in the aging brain (Uspenskaia, et al., 2004). In selected cases therefore, it may be beneficial to target cerebral microvessels in the basal lamina with the agents of the present invention in order to stimulate neoangiogenesis and increase blood flow and distribution in the brain.

Thus, in some embodiments, certain compounds of the invention, which are $\alpha 7$ nicotinic receptor agonists, may be used in the treatment of conditions that are treatable by the stimulation of angiogenesis. For example, in some embodiments, the condition to be treated is a wound. In particular embodiments, the wound is a diabetic ulcer. In other embodiments the wound is a non-healing wound in a non-diabetic individual. Additional conditions that may be treated include those described in U.S. Pat. Nos. 6,417,205 and 6,720,340, the disclosures of which are incorporated by reference herein in their entirety. For example, certain compounds of the invention, which are $\alpha 7$ nicotinic receptor agonists, may be used as a therapeutic approach to enhance angiogenesis in the treatment of coronary, peripheral, or other occlusive arterial diseases; and for the enhancement of wound healing and the improved vascularization of surgically transplanted tissues or organs (e.g., skin grafts or reattached limbs).

In particular embodiments, certain compounds of the invention, which are $\alpha 7$ nicotinic receptor antagonists, may be used in the treatment of conditions that are treatable by the inhibition of the $\alpha 7$ nicotinic receptor, including, for example, conditions that are treatable by the inhibition of angiogenesis (e.g., proliferative retinopathies, e.g., macular degeneration (including age-related, etc.; retinopathy of prematurity, etc.; and conditions associated with hyperproliferation, e.g., cancer, etc., including those conditions described in, for example WO03/068208, which is hereby incorporated by reference in its entirety).

For example, diseases and disorders amenable to treatment with the compounds of the invention, which are alpha7 nicotinic receptor antagonists, include, but are not limited to, cancer; atherosclerosis; proliferative retinopathies such as diabetic retinopathy; age-related maculopathy; retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other diseases and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

Inhibition of angiogenesis would be desirable in certain medical conditions, such as in tumor cell proliferation and in some forms of retinal (macular) degeneration. Alpha7 nAChR antagonists could be useful in inhibiting angiogenesis, as new blood vessel growth is necessary for growth of solid tumors. An anabaseine α7 nAChR antagonist that is polar, and/or ionized and/or conjugated to another inactive molecule such as a complex carbohydrate or a polyethylene glycol that confers on the molecule pharmacokinetic advantages and limits its diffusion to the compartment of administration may be useful as an angiogenesis inhibitor in treating certain conditions. Such an arylidene-anabaseine type α7 nAChR antagonist could also be directly administered into the arterial blood perfusing the tumor to achieve even greater selectivity of action.

Thus, in some embodiments, the compounds of the invention, which are α7 nicotinic receptor antagonists, may be used in the treatment of proliferative neuropathies.

In certain embodiments, the compounds of the invention, which are α7 nicotinic receptor antagonists, may be used in the treatment of proliferative diseases.

As used herein, the term "selectively binds," "selective binding," and cognates thereof refer to anabaseine compounds that preferentially bind one type of nicotinic acetylcholine receptor relative to another type of acetylcholine receptor (e.g., α7 nAChR versus the α4β2 nAChR). Because Ki is an inverse measure of affinity, binding selectivity of a compound for the α7 nAChR versus the α4β2 nAChR is expressed by dividing the Ki for binding to the α4β2 nAChR by the Ki for binding to the α7 nAChR. In one embodiment, a compound of the invention selectively binds α7 nAChR compared to α4β2 nAChR. The selectivity of a compound of the invention for α7 nAChR over α4β2 nAChR is at least 2, 3, 4, 5, 6, 7, 8, 9, 10, 11, 12, 13, 14, 15, or more. In another embodiment, a compound of the invention selectively binds α4β2 nAChR compared to α7 nAChR. The selectivity of a compound of the invention for α4β2 nAChR over α7 nAChR is at least 2, 3, 4, 5, 6, 7, 8, 9, 10, 11, 12, 13, 14, 15, or more. Binding to the α7 and α4β2 nAChR (including relative binding to each of these receptors) can be determined by the skilled artisan using the methods known in the art, in particular in view of the teachings provided herein. In particular, the assays used to determine selective binding are according to Marks and Collins for [$^{125}$I]alpha-bungarotoxin experiments (for alpha7 receptor binding) and a modified method by Pabreza et al. for [$^{3}$H]cytisine experiments (for α4β2), used as described in US 2009/0215705.

In certain embodiments, the compounds of the invention include, such as, 3-(DMXB)-4(R),6(S)-EA; 3-(4OHB)-4(R),6(S)-EA; 3-(DMXB)-4(S),6(R)-EA, dl-3-(4-Hydroxybenzylidene)-4,6-ethyleneanabaseine, 3-(Arylidene)-4,6-ethyl-ene-anabaseines, dl-3-(2,4-Dimethoxybenzylidene)-4,6-ethyleneanabaseine (free base), 3-(4-Hydroxy-3-methoxycinnamylidene)-4(R),6(S)-ethyleneanabaseine (free base), 3-(5-Acetoxyfurfurylidene)-4(R),6(S)-ethyleneanabaseine (free base), 3-(Benzo[b]thiophen-2-ylidene)-4(R),6(S)-ethyleneanabaseine (free base), and 3-(4-Aminobenzylidene)-4(R),6(S)-ethylene-anabaseine ("3-(4AminoB)-4(R),6(S)-EA").

In addition, the invention also includes compounds, such as, a) 3-(2,4-Dimethoxybenzylidene)-4(S)-methyl-anabaseine ("3-(DMXB)-4(S)-Me-A"):

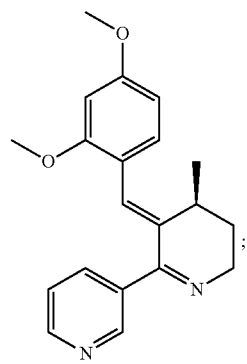 [SMILES: COc1ccc(/C=C2/C(c3cccnc3)=NCC[C@@H]2C)c(OC)c1]

b) 3-(2,4-Dimethoxybenzylidene)-dl-5-methyl-anabaseine (racemic mixture of "3-(DMXB)-5(R)-Me-A" and "3-(DMXB)-5(S)-Me-A"):

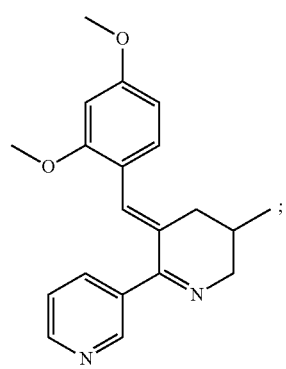

c) 3-(2,4-Dimethoxybenzylidene)-6(S)-methyl-anabaseine ("3-(DMXB)-6(S)-Me-A"):

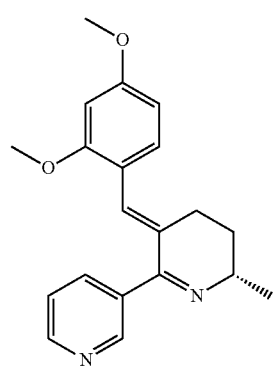

e) 3-(2,4-Dimethoxybenzylidene)-dl-4,6-dimethyl-anabaseine:

and f) 3-(4-Aminobenzylidene)-6(S)-methyl-anabaseine ("3-(4AminoB)-6(S)Me-A"):

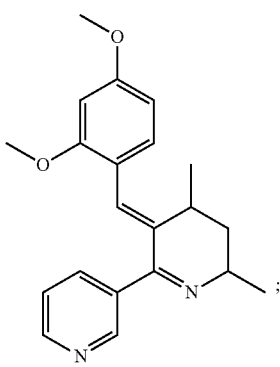

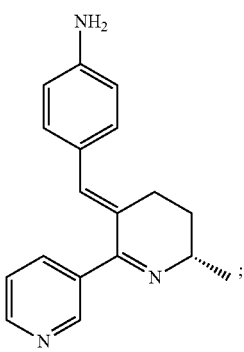 [SMILES: C[C@H]1CC/C(=C\c2ccc(N)cc2)C(c2cccnc2)=N1]

or a pharmaceutically acceptable salt, solvate, hydrate, clathrate, polymorph, stereoisomer, enantiomer, or combination thereof.

In a particular embodiment, the compound is 3-(DMXB)-4(R),6(S)-EA, or a pharmaceutically acceptable salt, solvate, hydrate, clathrate, polymorph, stereoisomer, enantiomer, or combination thereof.

In another embodiment, the compound is 3-(4-Aminobenzylidene)-4(R),6(S)-ethylene-anabaseine ("3-(4AminoB)-4(R),6(S)-EA"), or a pharmaceutically acceptable salt, solvate, hydrate, clathrate, polymorph, stereoisomer, enantiomer, or combination thereof.

Compositions, Formulations and Dosages

The compounds or pharmaceutical compositions or formulations thereof described herein will generally be used in an amount effective to achieve the intended result, for example in an amount effective to treat or prevent the particular condition being treated. The compounds or pharmaceutical compositions/formulations thereof may be administered therapeutically to achieve therapeutic benefit. By "therapeutic benefit" is meant eradication or amelioration of the underlying condition being treated and/or eradication or amelioration of one or more of the symptoms associated with the underlying condition such that the patient reports an improvement in feeling or condition, notwithstanding that the patient may still be afflicted with the underlying condition. Therapeutic benefit also includes halting or slowing the progression of the condition, regardless of whether improvement is realized.

The amount of the compositions/formulations administered in order to administer an effective amount of the compounds or pharmaceutical compositions/formulations thereof will depend upon a variety of factors, including, for example, the particular condition being treated, the frequency of administration, the particular compounds or pharmaceutical compositions/formulations thereof being administered, the severity of the condition being treated and the age, weight and general health of the individual, the adverse effects experienced by the individual being treated, etc. Determination of an effective dosage is within the capabilities of those skilled in the art in view of the teachings provided herein.

The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Compositions containing the compound(s) of the invention (and any additional pharmaceutical agent as described herein, e.g., a chemotherapeutic agent, anti-angiogenesis agent, pro-angiogenesis agent, etc.) may be administered in several ways, including orally, parenterally, intraperitoneally, intradermally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral dosage forms are also contemplated. Pharmaceutical compositions of the invention which are suitable for oral administration can be presented as discrete dosage forms, including, but not limited to, tablets (e.g., chewable tablets), caplets, capsules and liquids such as flavored syrups. Dosage forms containing predetermined amounts of active ingredients may be prepared by well-known methods of pharmacy. See, e.g., *Remington's Pharmaceutical Sciences* (1990) 18$^{th}$ ed., Mack Publishing Co., Easton, Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral, liquid, or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivates (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferable from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crosprovidone, polacrilin potassium, sodium starch glycolate, potato or tapioca starch, other starches, pre-gelatinized starch, other starches, clays, other algins, other cellulosses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The pH of a pharmaceutical composition or dosage form, or of the tissue where the composition or dosage form is applied, may be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients to improve delivery. Stearates for example can serve as a lipid vehicle for the formulation, as an emulsifying agent or surfactant, and as a delivery-enhancing or penetration-enhancing agent. Salts, hydrates or solvates of the active ingredients can be used to further adjust the properties of the resulting compositions.

Upon formulation, solutions are administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intradermal and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see, for example, *Remington's Pharmaceutical Sciences*, 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Kits

The invention provides kits for the treatment or prevention of diseases or disorders described herein In one embodiment, the kit includes a therapeutic or prophylactic composition containing an effective amount of a compound of the invention in unit dosage form. In some embodiments, a compound of the invention is provided in combination with a conventional therapeutic agent. In other embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, a compound of the invention is provided together with instructions for administering the compound to a subject having or at risk of developing a disease or disorder described herein. The instructions will generally include information about the use of the composition for the treatment or prevention of a disease or disorder described herein. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXEMPLIFICATION OF THE INVENTION

The following examples are put forth so as to provide those of ordinary skill in the art with a complete disclosure and description of how to make and use the assay, screening, and therapeutic methods of the invention, and are not intended to limit the scope of what the inventors regard as their invention.

I. Chemical Examples

Synthesis and Methods of Preparation

Compounds of the invention can be synthesized by methods described in this section, the examples, and the chemical literature.

A). Scheme for Preparation of Compounds of the Invention

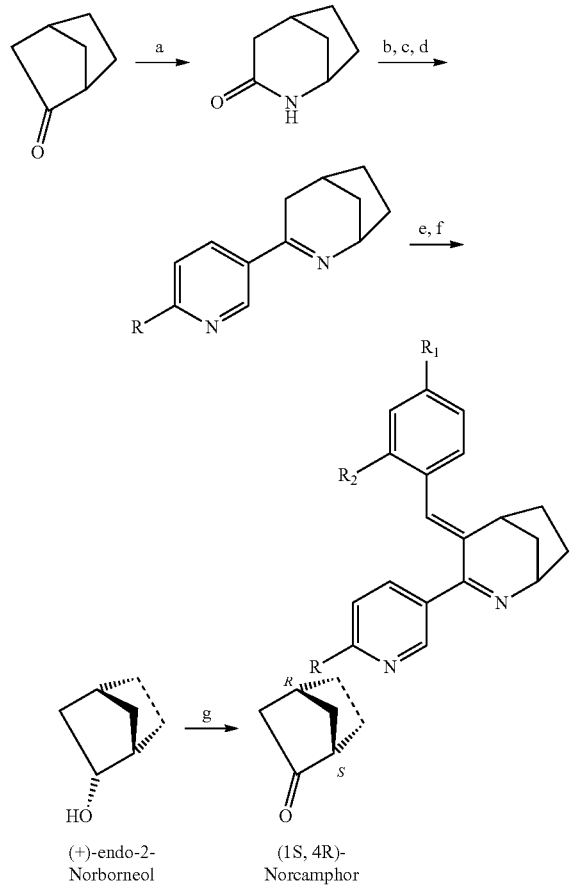

Scheme 1: Synthesis of 4,6-ethylene-anabaseine and 3-(arylidene)-4,6-ethyleneanabaseine compounds.

(+)-endo-2-Norborneol   (1S, 4R)-Norcamphor

Reagents:
(a) H$_2$N—O—SO$_3$H/AcOH, heat
(b) LDA/THF, ClSi(CH$_3$)$_3$, -78° C.
(c) LDA/THF, Et-nicotinate (R$_3$ = H)
(d) HCl, heat
(e) R$_1$,R$_2$-benzaldehyde/EtOH, HCl, heat
(f) Chiral chromatography
(g) PCC/CH$_2$Cl$_2$, 0° C.

The chiral precursor ((+)-endo-2Norcamphor) was used for the asymmetric synthesis of the pharmacologically potent and alpha7 selective enantiomer and for assignment of the configurations of both enantiomers obtained by chiral chromatography of the racemic 3-(DMXB)-4,6-ethyleneanabaseines.

Starting from commercially available racemic norcamphor, dl-4,6-ethylene-delta-valerolactam according to Krow et al. (1996) was prepared. The synthetic method for preparation of anabaseine hydrochloride as described in literature (Bloom, 1989; and Kem et al., 2004) was employed to obtain dl-4,6-ethyleneanabaseine. Its reaction with substituted benzaldehydes in acidic (1% concentrated HCl) ethanol at 70° C. overnight furnished 3-(4-hydroxybenzylidene)- and 3-(2,4-dimethoxybenzylidene)-dl-4,6-ethylene-anabaseines, which were subsequently separated by chiral HPLC into their enantiomers for pharmacological evaluation.

Because the absolute configuration of the potent, selective chiral compound isolated by chiral HPLC was not known, asymmetric synthesis was used to obtain one of the two possible chiral forms and for identification of the pharmacologically most active compound. The synthesis could start with norcamphor, but since the two chiral forms of norcamphor were not commercially available, (+)-endo-2-norborneol (Aldrich, USA) was used to obtain the desired (1S, 4R)-norcamphor by oxidation (Herscovici et al. 1982; Kawamura et al., 1995; Lattanzi et al., 2004). From (1S,4R)-norcamphor, 4(R),6(S)-4,6-ethyleneanabaseine was obtained using essentially the same method as those for anabaseine synthesis. The NMR spectra of the chiral intermediates and end product were identical with the spectra initially obtained with the racemic compounds.

B). Synthesis of dl-4,6-ethyleneanabaseine and 4(R),6 (S)-ethyleneanabaseine

Commercially available chemicals were purchased from Fisher Scientific and Sigma-Aldrich and used without any further purification. All glassware was dried overnight in an oven at 120° C. Synthesis of dl-4,6-ethylene-anabaseine was carried out in an argon atmosphere. After 7.5 ml of dry tetrahydrofuran (THF) was cooled to -75° C., 5.1 ml (9.2 mmole) of 1.8 M LDA solution in heptane/THF/ethylbenzene was added drop by drop over a period of 5 minutes. When this solution was cooled again to -75° C., 1.16 g (9.3 mmole) 2-aza-3-oxo-bicyclo[3.2.1]octane (Krow at al. 1996) in 4.0 ml THF was added over 20 minutes (The 2-aza-3-oxo-bicyclo [3.2.1]octane was dried before use by distilling 2×10 ml dry benzene at 55° C. in vacuum). When the solution was cooled again to -75° C., 1.16 ml (1.00 g, 9.2 mmole) chlorotrimethylsilane was added drop by drop over 5 minutes.

The reaction mixture was then stirred at -75° C. for 15 minutes and at room temperature for 2 hours. It was cooled down again to -75° C. and 5.1 ml (9.2 mmole) of 1.8 M LDA solution in heptane/THF/ethylbenzene was added drop by drop over 10 minutes. After stirring for 20 minutes at -75° C., 0.96 ml (1.05 g, 7.0 mmole) of ethyl nicotinate was added drop by drop over 5 minutes. The reaction mixture was stirred at -75° C. for 20 minutes and then at room temperature overnight. Then 10 ml of water was added and the mixture was stirred at room temperature for 1 hour; after phase separation the organic phase was washed with 1 ml water, the combined aqueous phases were washed with 10 ml of hexane and evaporated at 50° C. under vacuum. To the ice cooled residue (2.86 g), 10 ml of ice cold concentrated hydrochloric acid was added and the resulting solution was boiled (with stirring) in an oil bath at 105° C. for 18 hours. The brown solution was then evaporated at 40° C. using a membrane vacuum pump; to the oily residue a pH 8.0 saturated sodium bicarbonate solution and later a 1 N sodium hydroxide solution was added, and this basic aqueous phase was then extracted with 5×10 ml chloroform. The combined chloroform solutions were decolorized with activated carbon, dried over magnesium sulfate and evaporated in vacuum at 30° C.

The residue (1.065 g) was chromatographed on silica gel (75 g) with cyclohexane-diethylamine (8:2, v/v), giving the expected product (0.125 g, yield 7.2%). $^1$H-NMR (300 MHz, CDCl$_3$, delta, TMS int. standard): 8.91 (1H, dd, J=2.1, 1.2 Hz), 8.60 (1H, dd, J=4.8, 1.8 Hz), 8.08 (1H, dt, J=8.1, 1.8 Hz), 7.29 (1H, ddd, J=7.8, 4.8, 0.9 Hz), 4.44-4.39 (1H, m), 2.99 (1H, ddd, J=18.6, 5.1, 2.1 Hz), 2.61-2.51 (2H, m), 2.04-1.77 (4H, m), 1.67-1.53 (2H, m). $^{13}$C-NMR (75 MHz, CDCl3, delta, TMS int. standard): 162.1, 150.5, 147.5, 134.6, 133.3, 123.1, 58.5, 40.1, 34.7, 33.9, 31.7, 31.0.

C) Synthesis of 1(S),4(R)-Norcamphor

A mixture of 12.93 g (0.060 mol) pyridinium chlorochromate and dry methylenedichloride (130 ml) was cooled in an ice bath then molecular sieves (3AO, 30 g) and (+)-endo-2-norborneol (3.37 g, 0.030 mol) was added and stirred in an ice bath for 2 hours. Dry ether (400 ml) was added to the reaction mixture at room temperature, stirred for 30 minutes and decanted. The solid residue was treated with dry ether (50 ml), stirred for 15 minutes and decanted; this procedure was repeated three times. The combined decanted solutions were combined, filtered through a silica gel layer (1 cm high on a glass filter) and evaporated with a rotavapor, giving the desired product. $^1$H-NMR (300 MHz, CDCl$_3$, delta, TMS int. standard): 2.67 (1H, br s), 2.60 (1H, br s), 2.06 (1H, dd, J=18.0, 2.4 Hz), 1.86 (1H, d, J=4.2 Hz), 1.84-1.77 (2H, m), 1.73 (1H, dt, J=10.2, 1.5 Hz), 1.59-1.49 (2H, m), 1.48-1.39 (1H, m). $^{13}$C-NMR (75 MHz, CDCl$_3$, delta, TMS int. standard): 218.3, 49.8, 45.2, 37.7, 35.3, 27.2, 24.2.

D) Synthesis of (4R,6S)-Ethylene-δ-valerolactam

To a solution of (1S,4R)-norcamphor (2.75 g 0.025 mole) in glacial acetic acid (150 ml) hydroxylamine-O-sulfonic acid (4.52 g, 0.040 mole) was added and stirred in an oil bath of 125° C. for 2 hours. After cooling down the mixture was evaporated on rotavapor at 25° C., saturated aqueous sodium bicarbonate solution (60 ml) was added slowly and carefully to the residue (11.6 g) during stirring, then solid sodium bicarbonate (10 g) was added in small portions to pH 7.5 and extracted with chloroform (6×10 ml). The combined extracts were dried over magnesium sulfate decolorized with activated carbon and evaporated at 35° C., giving the crude product (2.59 g), which was purified by column chromatography on silica gel (150 g) with ether containing 20% of ethanol. $^1$H-NMR (300 MHz, CDCl$_3$, delta, TMS int. standard): 6.77 (1H, br s), 3.55-3.53 (1H, m), 2.62-2.47 (2H, m), 2.29-2.20 (1H, m), 2.07-1.57 (6H, m). $^{13}$C-NMR (75 MHz, CDCl$_3$, delta, TMS int. standard): 172.1, 53.0, 41.9, 36.1, 35.3, 32.4, 32.1, 28.9.

E) Synthesis of (4R,6S)-Ethyleneanabaseine 10 ml dry THF was cooled to −75° C. and 5.81 ml (10.5 mmole) 1.8 M LDA solution in heptane/THF/ethylbenzene was added drop by drop in 5 minutes. When it cooled down to −75° C. a solution of 1.32 g (10.5 mmole) (4R,6S)-4,6-ethylene-delta-valerolactam in 20 ml THF was added in 20 minutes (the lactam was dried before use by distilling 2×10 ml dry benzene at 55° C. in vacuum). When the solution cooled down again under −75° C. 1.32 ml (1.14 g, 10.5 mmole) chlorotrimethylsilane was added drop by drop over 5 minutes. The reaction mixture was stirred at −75° C. for 15 minutes and at room temperature for 2 hours. It was cooled down again to −75° C. and 5.81 ml (10.5 mmole) 1.8 M LDA solution in heptane/THF/ethylbenzene was added drop by drop in 8 minutes. After stirring for 20 minutes at −75° C. 1.09 ml (1.21 g, 8.0 mmole) ethyl nicotinate was added drop by drop in 5 minutes. The reaction mixture was stirred at −75° C. for 25 minutes and at room temperature overnight (16 hours). Then 1 ml of water was added and stirred at room temperature for 2 hours, the separated material was filtered, washed with dry THF (2×15 ml) and it was added, during stirring, into 10 ml of ice cold concentrated hydrochloric acid and boiled in an oil bath at 105° C. for 18 hours.

The brown solution was evaporated at 40° C. using a membrane vacuum pump; to the oily residue saturated sodium bicarbonate and 1 N sodium hydroxide solution were added to pH 8 and it was then extracted with 5×5 ml chloroform. The combined chloroform solution were decolorized with activated carbon, dried over magnesium sulfate and evaporated in vacuum at 30° C. The residue (1.67 g) was chromatographed on silica gel (100 g) with cyclohexane-diethylamine (8:2, v/v) then on 20 g silica gel with ether-diethylamine (95-5 v/v) giving the expected product (0.110 g, 5.6%). $^1$H-NMR (300 MHz, CDCl$_3$, delta, TMS int. standard): 8.90 (1H, dd, J=2.4, 0.6 Hz), 8.59 (1H, dd, J=4.8, 1.8 Hz), 8.08 (1H, J=7.8, 2.1 Hz), 7.29 (1H, ddd, J=8.1, 4.8, 0.9 Hz), 4.43-4.38 (1H, m), 2.99 (1H, ddd, J=18.6, 5.2, 2.1 Hz), 2.62-2.51 (2H, m), 2.04-1.77 (4H, m), 1.68-1.53 (2H, m). $^{13}$C-NMR (75 MHz, CDCl3, delta, TMS int. standard): 162.1, 150.5, 147.5, 134.6, 133.3, 123.2, 58.5, 40.1, 34.7, 33.9, 31.

F) Synthesis of dl-3-(4-Hydroxybenzylidene)-4,6-ethyleneanabaseine

To a mixture of 32 mg (0.172 mmol) dl-4,6-ethyleneanabaseine and 25 mg (0.206 mmol) 4-hydroxybenzaldehyde in 1 ml of dry ethanol, 2 drops of concentrated hydrochloric acid was added and the mixture (under argon in a closed flask) was stirred overnight (18 hours) in an oil bath of 83-85° C. After cooling, the reaction mixture was evaporated, 1 ml saturated sodium bicarbonate and 12 drops of 12% sodium hydroxide solution were added to the residue to yield a pH of 8.0 and it was extracted with 5×1 ml of dichloromethane. The combined extracts were died over magnesium sulfate, decolorized with activated carbon and evaporated.

The residue (27.7 mg) was purified by column chromatography on silica gel (3 g) with dichloromethane-methanol (9:1, v/v) giving the pure compound. $^1$H-NMR (300 MHz, CDCl$_3$, delta, TMS int. standard): 8.65 (1H, dd, J=2.4, 0.9 Hz), 8.62 (1H, dd, J=4.8, 1.8 Hz), 7.80 (1H, dt, J=8.1, 2.1 Hz), 7.38 (1H, ddd, J=7.5, 4.8, 0.9), 7.15 (2H, d, J=8.7 Hz), 6.79 (2H, d, J=8.7 Hz), 6.36 (1H, s), 4.42 (1H, br s), 3.61 (1H, t, J=5.1 Hz), 2.30-2.17 (1H, m), 2.08-1.99 (2H, m), 1.93-1.81 (2H, m), 1.71-1.61 (1H, m).

G) Synthesis of 3-(2,4-Dimethoxybenzylidene)-4(S)-methyl-anabaseine

1) N-BOC-4(S)-methyl-piperid-2-one

4-Dimethylamino-pyridine (0.61 g, 0.005 mole) and 4(S)-methyl-piperid-2-one (0.65 g, 0.00575 mole) were added under argon atmosphere to a solution of di-tert-butyl dicarbonate (2.18 g, 0.010 mole) in dry dichloromethane (10 ml) triethylamine (0.61 g, 0.005 mole), and stirred at room temperature overnight. The reaction mixture was evaporated on rotavapor at 55° C. and the residue (1.609 g) was purified by silica gel (40 g) column chromatography eluting with ethyl acetate, furnishing the pure product (0.673 g, 55% yield). 1H-NMR (300 MHz, CDCl3, delta, TMS int. standard): 3.84-

3.75 (1H, m), 3.55-3.44 (1H, m), 2.64-2.50 (1H, m), 2.17-2.06 (1H, m), 2.05-1.87 (2H, m), 1.53 (9H, s), 1.50-1.37 (1H, m), 1.02 (3H, d, J=6.3 Hz).

2) 4(S)-Methyl-anabaseine

All glassware was dried in an oven at 120° C. for 24 hours and the reaction was carried out in argon atmosphere. A stirred solution of 3-bromo-pyridine (0.30 ml, 0.49 g, 3.11 mmol) in dry ether (8.5 ml) was cooled to −78° C. (with dry ice/acetone) and during stirring n-butyl lithium solution (1.6 M in hexane, 1.95 ml, 3.12 mmol) was added dropwise, then the solution was stirred for an additional 30 minutes. To this stirred and cooled solution N-BOC-6(S)-methyl-piperid-2-one (0.619 g, 2.90 mmol, dried beforehand by distilling 10 ml of dry benzene on a rotavapor at 55° C. from it) in dry tetrahydrofuran (7 ml) was added drop by drop during 1 hour. This reaction mixture was stirred at −78° C. for 3 hours then 2N hydrochloric acid (3.1 ml, 6.2 mmol) was slowly added drop wise during 10 minutes and the stirred reaction mixture was left to warm up to room temperature.

After separation the aqueous phase was extracted with ether (3×10 ml), the combined organic solutions were washed with 1×5 ml saturated sodium bicarbonate solution and 2×4 ml brine, dried (magnesium sulfate) and evaporated at 30° C. Trifluoroacetic acid (3.0 ml) was added at ice cooling and stirring under argon atmosphere to the residue (0.943 g) which was then stirred at room temperature for 18 hours. After evaporation on a rotavapor at 30° C. an aqueous sodium hydroxide solution (40%) was added to the residue drop wise to attain pH 10 at ice cooling while stirring, then extracted with diethyl ether (1×10 and 4×5 ml). The combined organic solutions were dried (magnesium sulfate) and evaporated on rotavapor at 45° C. in good vacuum giving the crude product (0.236 g, 47% yield) from which the analytical sample was prepared by column chromatography on silica gel with cyclohexane containing 30% triethylamine (0.083 g, 5% Yield). 1H-NMR (300 MHz, CDCl3, delta, TMS int. standard): 8.96 (1H, dd, J=2.1, 0.3 Hz), 8.61 (1H, dd, J=4.8, 1.8 Hz), 8.10 (1H, dt, J=8.1, 2.1 Hz), 7.31 (1H, ddd, J=8.1, 4.8, 0.9 Hz), 4.09 (1H, dm, J=18.0 Hz), 3.79-3.65 (1H, m), 2.85-2.75 (1H, dm, J=17.7 Hz), 2.18-2.06 (1H, m), 1.97-1.74 (2H, m), 1.35-1.21 (1H, m), 1.08 (3H, d, J=6.6 Hz).

3) 3-(2,4-Dimethoxybenzylidene)-4(S)-methyl-anabaseine bishydrochloride 2,4-Dimethoxy-benzaldehyde (0.0415 g, 0.25 mmol) and concentrated hydrochloric acid (2 drops) were added to a solution of 4(S)-methyl-anabaseine (0.036 g, 0.21 mmol) in dry ethanol (1.5 ml) and the reaction mixture (pH~1) was stirred under argon atmosphere in a closed system in an 82° C. bath for 16 hours. After standing in a refrigerator at 4° C. for 2 days it was filtered and washed with cold ethanol under dry argon atmosphere, then dried in a desiccator over phosphorous pentoxide, furnishing the very hygroscopic pure product (0.011 g, 13% yield). 1H-NMR (300 MHz, DMSO-d6, delta, TMS int. standard): 8.90 (1H, dd, J=4.8, 1.5 Hz), 8.84 (1H, d, J=1.5 Hz), 8.10 (1H, dt, J=7.8, 1.8 Hz), 7.70 (1H, dd, J=7.8, 4.8 Hz), 7.66 (1H, d, J=8.7 Hz), 7.27 (1H, s), 6.74 (1H, dd, J=8.7, 2.4 Hz), 6.64 (1H, d, J=2.4 Hz), 3.86 (3H, s), ~3.8 (2H, under the water line), 3.69 (3H, s), 3.51-3.43 (1H, m), 2.21-1.89 (2H, m), 1.35 (3H, d, J=6.6 Hz).

H) Synthesis of 3-(2,4-dimethoxybenzylidene-dl-5-methyl-anabaseine 1) dl-5-Methyl-anabaseine bishydrochloride A solution containing dl-5-methyl-piperid-2-one 2.00 g, 17.7 mmol), aqueous formaldehyde solution (37%, 1.7 ml, 21 mmol) and diethyl amine (2.2 ml, 21 mmol) was stirred and refluxed in a 115° C. oil bath for 8 hours, then evaporated on a rotavapor at 50° C. in good vacuum. To the crude N-diethylaminomethyl-5 methyl-piperid-2-one residue (2.13 g, 10.7 mmol) dry toluene (10 ml), ethyl nicotinate (1.62 g, 10.7 mmol) and (in portions) sodium hydride (60% in mineral oil, 0.88 g, 22.0 mmol) were added and refluxed with stirring for 4 hours. Additional sodium hydride dispersion (0.44 g, 11.0 mmol) was added to the reaction mixture and stirred and refluxed for an additional 4 hours. After cooling to room temperature the excess sodium hydride was filtered (and carefully destroyed), the filtrate was cooled with ice overnight. The precipitated material was filtered, washed with hexane, then boiled in a mixture of concentrated hydrochloric acid (5 ml) and acetone (1 ml) overnight. After cooling, the separated sodium chloride was removed by filtration and isopropanol (40 ml) was added, cooled at 5° C. for 3 days while the dihydrochloride salt of the product (0.17 g, 4% yield) slowly separated. 1H-NMR (300 MHz, DMSO-d6, delta, TMS int. standard): 9.27 (1H, dd, J=2.1, 0.6 Hz), 8.91 (1H, dd, 5.1, 1.5 Hz), 8.56 (1H, dt, J=8.1, 2.1 Hz), 7.80 (1H, ddd, J=8.1, 5.1, 0.6 Hz), 3.29-3.07 (2H, m), 2.89-2.73 (1H, m), 2.70-2.59 (1H, m), 1.92-1.67 (2H, m), 1.60-1.45 (1H, m), 0.98 (3H, d, J=6.6 Hz).

2) 3-(2,4-Dimethoxybenzylidene)-dl-5-methyl-anabaseine

A solution containing dl-5-methyl-anabaseine bis hydrochloride (0.17 g, 0.64 mmol), 2,4-dimethoxybenzaldehyde (0.14 g, 0.83 mmol) in ethanol (5 ml) and concentrated hydrochloric acid (2 drops) was boiled overnight on a 75° C. oil bath. After evaporation on the rotavapor the residue (0.35 g) was dissolved in water (5 ml), sodium bicarbonate (0.5 g) was added to saturation and the aqueous solution was extracted with dichloromethane (3×5 ml). The combined extracts were died (magnesium sulfate), evaporated and the residue (0.17 g) was purified by column chromatography on silica gel (25 g) with benzene-hexane-diethylamine (9-4-1), furnishing the pure product (0.0616 g, 30% yield). 1H-NMR (300 MHz, CDCl3, delta, TMS int. standard): 8.75 (1H, dd, J=2.1, 0.9 Hz), 8.61 (1H, dd, J=4.8, 1.8 Hz), 7.82 (1H, dt, J=4.8, 2.1 Hz), 7.30, (1H, ddd, J=7.8, 4.8, 0.9 Hz), 7.25 (1H, d, J=8.4 Hz), 6.78 (1H, s), 6.51 (1H, dd, J=8.7, 2.4 Hz), 6.43 (1H, d, J=2.4 Hz), 4.05 (1H, dm, J=17.4 Hz), 3.82 (3H, s), 3.72 (3H, s), 3.35 (1H, dd, J=17.4, 9.9 Hz), 2.90 (1H, dm, J=15.0 Hz), 2.29-2.18 (1H, m), 1.96-1.81 (1H, m), 1.02 (3H, d, J=6.6 Hz).

I) Synthesis of 3-(2,4-Dimethoxybenzylidene)-6(S)-methyl-anabaseine

1) N-BOC-6(S)-methyl-piperid-2-one

Ruthenium(IV) oxide hydrate (0.8 g, 0.006 mol) then a solution of N-BOC-6(S)-methyl-piperidine (4.00 g, 0.020 mol) in ethyl acetate (240 ml) were added to a solution of sodium periodate (21.36 g, 0.100 mole) in water (200 ml) and strongly stirred for 24 hours at room temperature under argon atmosphere. After separation the aqueous phase was extracted with ethyl acetate (3×100 ml). The combined organic phases were dried with magnesium sulfate and then treated with activated carbon, giving a colorless solution that was evaporated on a rotavapor at 30° C. The residue (3.98 g) was purified by silicagel (125 g) column chromatography with cyclohexane-ethyl acetate (1-1, v/v), furnishing a product (2.50 g, 59% yield) which according to its $^1$H-NMR spectrum was pure enough for the next reaction step.

2) 6(S)-Methyl-anabaseine

All glassware was dried in an oven at 120° C. for 24 hours and the reaction was carried out in argon atmosphere. A stirred solution of 3-bromo-pyridine (0.70 g, 4.4 mmol) in dry ether (12 ml) was cooled to −78° C. (with dry ice/acetone); n-butyl lithium solution (1.6 M in hexane, 2.75 ml, 4.4 mmol) was added dropwise during stirring, then the solution was stirred for an additional 30 minutes. To the cooled solution N-BOC-6(S)-methyl-piperid-2-one (0.935 g, 4.4 mmol, dried before by distilling 10 ml of dry benzene on a rotavapor at 55° C. from it) in dry tetrahydrofuran (7 ml) was added drop by drop during 1 hour. This reaction mixture was stirred at −78° C. for 3 hours, then 2N hydrochloric acid (4.4 ml, 8.8 mmol) was slowly added drop wise over 10 minutes and the stirred reaction mixture was left to warm up to room temperature. After separation the aqueous phase was extracted with ether (3×15 ml), the combined organic solutions were washed with 1×5 ml saturated sodium bicarbonate solution and 2×5 ml brine, dried (magnesium sulfate) and evaporated at 30° C. Trifluoroacetic acid (3.5 ml) was added to this residue (0.812 g) during ice cooling and stirring under argon atmosphere, then stirred at room temperature for an additional 4 hours. After evaporation on the rotavapor at 30° C., aqueous sodium hydroxide solution (40%) was added dropwise to the residue with ice cooling and stirring to attain a pH of 12 and this was extracted with diethyl ether (1×10 and 4×5 ml). The combined organic solutions were dried (magnesium sulfate) and evaporated on rotavapor at 30° C. in good vacuum giving the raw product (0.192 g, 25%) from which the analytical sample was prepared by column chromatography on silica gel with cyclohexane containing 30% triethylamine. $^1$H-NMR (300 MHz, CDCl$_3$, delta, TMS int. standard): 8.95 (1H, dd, J=2.4, 0.6 Hz), 8.61 (1H, dd, J=4.8, 1.5 Hz), 8.12 (1H, dt, J=7.8, 2.1 Hz), 7.31 (1H, ddd, J=8.1, 4.8, 0.9 Hz), 3.78-3.64 (1H, m), 2.65-2.59 (1H, m), 2.57-2.44 (1H, m), 2.02-1.68 (3H, m), 1.36 (3H, d, J=6.9 Hz), 1.32-1.1.24 (1H, m).

3) 3-(2,4-Dimethoxybenzylidene)-6(S)-methyl-anabaseine 2,4-Dimethoxy-benzaldehyde (0.0415 g, 0.25 mmol) and concentrated hydrochloric acid (2 drops) were added to a solution of 6(S)-methyl-anabaseine (0.037 g, 0.21 mmol) in dry ethanol (1.5 ml) and the reaction mixture (pH~1) was stirred under argon atmosphere in a closed system in an 82° C. bath for 16 hours. The pure product free base was obtained by isocratic silica gel semipreparative HPLC using 90% hexane-10% isopropanol solvent for elution (0.021 g, 26 yield %). $^1$H-NMR (300 MHz, CDCl$_3$, delta, TMS int. standard): 8.75 (1H, dd, J=2.1, 0.6 Hz), 8.61 (1H, dd, J=4.8, 1.8 Hz), 7.83 (1H, dt, J=7.8, 2.1 Hz), 7.31 (1H, ddd, J=7.8, 4.8, 0.6 Hz), 7.27 (1H, d, J=7.2 Hz), 6.77 (1H, s), 6.50 (1H, dd, J=8.4, 2.4 Hz), 6.42 (1H, d, J=2.1 Hz), 3.83 (3H, s), 3.82-3.66 (1H, m), 3.71 (3H, s), 2.86 (1H, dm, 15.6 Hz), 2.69-2.54 (1H, m), 2.10-1.88 (1H, m), 1.55-1.42 (1H, m), 1.41 (3H, d, J=6.6 Hz).

J) Synthesis of the cis and trans isomers of 3-(2,4-dimethoxybenzylidene)-dl-4,6-dimethyl-anabaseine 1) dl-2,4-Dimethyl-piperidine According to Ogawa et al. (1984), 2,4-dimethyl-pyridine (5.00 g) was used to prepare 2,4-dimethyl-piperidine (3.53 g, 67% yield). It was 95% pure according to its $^1$H-NMR spectrum and contained the cis- and trans-isomers in about 29-71 ratio. (Reference: Ogawa, K., Takeuchi, Y., Suzuki, H. and Nomura, Y. (1984). Barriers to Rotation and Inversion in meso-1,1'-Bi(2-methylpiperidine)s. Journal of the American Chemical Society 106 (4), 831-841)

2) dl-N-BOC-2,4-dimethyl-piperidine

Di-tert-butyl dicarbonate (6.95 g, 0.032 mole) and triethylamine (4.06 ml, 0.0291 mole) were added to a solution of dl-2,4-dimethyl-piperidine (3.53 g, 0.0312 mole) in 1,4-dioxane (40 ml)-water (40 ml), and the suspension was strongly stirred at room temperature for 24 hours. The reaction mixture was acidified with 2N hydrochloric acid to pH 4 and extracted with ether (4×25 ml). The combined organic extracts were dried (magnesium sulfate), evaporated on rotavapor at 30° C. and purified by column chromatography on silica gel with cyclohexane containing 10% of ethyl acetate, furnishing product (5.37 g, 81% yield) which was pure enough for the next step (According to its $^1$H-NMR spectrum it contained the cis- and trans-isomers in about 22% and 78% respective molar proportions).

3) dl-N-BOC-4,6-dimethyl-piperid-2-one

To a solution of sodium periodate (26.7 g, 0.125 mole) in water (250 ml) at room temperature with strong stirring under argon atmosphere, ruthenium(IV) oxide hydrate (1.0 g, 0.0075 mole) was added, then a solution of dl-N-BOC-2,4-piperidine (5.37 g, 0.025 mole) in ethyl acetate (300 ml) was added and the mixture was stirred for 24 hours. After phase separation the aqueous phase was extracted with ethyl acetate (3×100 ml). The combined organic phases were dried (magnesium sulfate) and treated with activated carbon giving a colorless solution which was evaporated on rotavapor at 30° C. The residue (5.80 g) was purified by column chromatography on silicagel (125 g) with cyclohexane containing 30% of ethyl acetate furnishing the pure product (2.61 g, 46%) which according to its $^1$H-NMR spectrum consisting its cis- and trans isomers and pure enough for the next reaction step.

4) dl-4,6-Dimethyl-anabaseine

All glassware was dried in an oven at 120° C. for 24 hours and the reaction was carried out in argon atmosphere. N-butyl lithium solution (1.6 M in hexane, 7.15 ml, 11.4 mmol) was added drop wise with stirring to a solution of 3-bromo-pyridine (1.80 g, 11.4 mmol) in dry ether cooled to −78° C. (with dry ice/acetone); this solution was then stirred for an additional 30 minutes. To this cooled solution, dl-N-BOC-4,6-dimethyl-piperid-2-one (2.59 g, 11.4 mmol, dried before by distilling 12 ml of dry benzene on a rotavapor at 55° C.) in dry tetrahydrofuran (20 ml) was added drop by drop over 1 hour. This reaction mixture was then stirred at −78° C. for 3 hours. Then 2N hydrochloric acid (11.5 ml, 23.0 mmol) was slowly added dropwise over 20 minutes and the stirred reaction mixture was left to warm up to room temperature. After separation the aqueous phase was extracted with ether (3×40 ml), the combined organic solutions were dried (magnesium sulfate) and evaporated at 30° C. atmosphere. Trifluoroacetic acid (11 ml, 144 mmol) was added to this residue (2.25 g) during ice cooling and stirring under argon, then stirred at room temperature overnight. After evaporation on the rotavapor at 30° C., aqueous sodium hydroxide solution (40%) was added dropwise to the residue while being cooled with and being stirred until pH 10-11 was attained and then extracted with dichloromethane (10×20 ml). The combined organic solutions were dried (magnesium sulfate) and evaporated on the rotavapor at 30° C. in good vacuum, giving the crude cis-trans isomer mixture (1.34 g, 7.12 mmol, 62% yield), which is not stable except at low temperature (it can be stored at −78° C.), so it was used without purification at the next step.

5) 3-(2,4-Dimethoxybenzylidene)-dl-cis- and trans-4,6-dimethyl-anabaseine 2,4-Dimethoxy-benzaldehyde (0.069 g, 0.345 mmol) and concentrated hydrochloric acid (2 drops) were added to a solution of 4,6-dimethyl-anabaseine isomer mixture (0.065 g, 0.345 mmol) in dry ethanol (2 ml) and the reaction mixture (pH~1) was stirred under argon atmosphere in a closed system in an 82° C. bath for 16 hours. It was evaporated on the rotavapor at 30° C. Then water (0.5 ml), potassium bicarbonate (0.2 g) and chloroform (1 ml) were added to the residue, which then separated into two phases; the aqueous phase was extracted with chloroform (3×1 ml). The combined organic phases were dried (magnesium sulfate) and evaporated on the rotavapor at 30° C. The residue (0.130 g) was column chromatographed on silica gel (10 g) with ether containing 10% of triethylamine collecting fractions of 2-3 ml.

The Rf=0.41 fractions containing the compound of were combined and evaporated, giving the pure cis-isomer (3.2 mg). $^1$H-NMR (300 MHz, CDCl$_3$, delta, TMS int. standard): 8.64 (1H, dd, J=2.4, 0.9 Hz), 8.30 (1H, dd, J=4.8, 1.5 Hz), 7.77 (1H, dt, J=6.9, 0.9 Hz), 6.98 (1H, ddd, J=7.8, 4.8, 0.9), 6.80 (1H, s), 6.63 (1H, dd, J=8.4, 0.6 Hz), 6.15 (1H, d, J=2.7 Hz), 6.05 (1H, dd, J=8.1, 2.4 Hz), 3.75 (3H, s), 3.64 (3H, s), 3.51-3.37 (1H, m), 2.96-2.82 (1H, m), 2.20 (1H, ddd, J=13.2, 7.5, 4.2 Hz), 1.51 (3H, d, J=6.6 Hz), 1.23 (3H, d, J=7.2 Hz), 1.05 (1H, ddd, J=13.2, 11.4, 9.3 Hz)

Similarly, the Rf=0.27 fractions were combined and evaporated giving the pure trans-isomer (8.4 mg). $^1$H-NMR (300 MHz, CDCl$_3$, delta, TMS int. standard): 8.74 (1H, d, J=2.4 Hz), 8.59 (1H, dd, J=5.1, 1.8 Hz), 7.82 (1H, dt, J=8.1, 2.1 Hz), 7.29 (1H, dd, J=7.8, 5.1 Hz), 7.28 (1H, d, J=9.0 Hz), 6.65 (1H, s), 6.51 (1H, dd, J=8.7, 2.4 Hz), 6.42 (1H, d, J=2.4 Hz), 3.83 (3H, s), 3.71 (3H, s), 3.25-3.14 (1H, m), 1.76 (1H, ddd, J=13.5, 4.5, 3.0 Hz), 1.57 (1H, ddd, J=13.5, 11.1, 4.2 Hz), 1.40 (3H, d, J=6.9 Hz), 1.29 (3H, d, J=7.2 Hz), 1.17-1.07 (1H, m).

By repeated column or HPLC chromatography further cis- and trans-product can be obtained from the other column fractions. Interpretation of the couplings of the methylene protons with the adjacent protons, using their coupling constants, it was possible to determine which fraction contained the cis- and which contained the trans-product.

K) Synthesis of 3-(4-Aminobenzylidene)-6(S)-methyl-anabaseine 3-(4-Aminobenzylidene)-6(S)-methyl-anabaseine 4-Aminobenzaldehyde (0.030 g, 0.25 mmol) in 2.0 ml ethanol containing two drops of conc. HCl was added to 6(S)-methyl-anabaseine free base (0.021 g, 0.12 mmol) and the solution was heated at 70° C. overnight. Solvent was then removed with the rotavapor and the resulting residue was dissolved in 5 ml water (pH attained was 2.5) and then extracted 4×15 nil diethylether to remove byproducts and unreacted aldehyde. The pH of the aqueous solution was raised to >12 and it was then extracted again 3×15 ml diethylether and once with chloroform. The resulting organic phases were evaporated with rotovapor and the desired product was obtained from the resulting residue by semipreparative HPLC on silica gel column (0.008 g., 21% yield). $^1$H-NMR (300 MHz, CDCl$_3$, delta, TMS int. standard): 8.72 (1H, s), 8.61 (1H, d, J=4.5 Hz), 7.80 (1H, dm, J=7.8 Hz), 7.31 (1H, dd, J=7.8, 5.1 Hz), 7.15 (2H, d, J=8.4 Hz), 6.65 (2H, d, J=8.4 Hz), 6.50 (1H, s), 3.71-3.57 (1H, m), 2.95 (1H, dm, J=16.5 Hz), 2.79-2.65 (1H, m), 2.02-1.92 (1H, m), 1.51-1.34 (1H, m), 1.41 (3H, d, J=6.9 Hz). HRMS (+E SI): theoretical for [M+H]$^+$=278.1652. found: 278.1654.

L) Synthesis of 3-(4-Aminobenzylidene)-4(R),6(S)-ethylene-anabaseine 3-(4-Aminobenzylidene)-4(R),6(S)-ethylene-anabaseine 4-Aminobenzaldehyde (0.033 g, 0.27 mmol) in 2.0 ml ethanol containing two drops of conc. HCl was added to 4(R),6(S)-ethylene-anabaseine free base (0.025 g, 0.134 mmol) and the solution was heated at 70° C. overnight. Solvent was then removed with the rotavapor and the resulting residue was dissolved in 5 ml water (pH attained was 2.5) and then extracted 4×15 ml diethylether to remove byproducts and unreacted aldehyde. The pH of the aqueous solution was then raised to >12 and it was then extracted again 3×15 ml diethylether and once with chloroform. The resulting organic phases were evaporated with rotovapor and the desired product was obtained from the resulting residue by semipreparative HPLC on silica gel column (0.0101 g, 26% yield). $^1$H-NMR (300 MHz, CDCl$_3$, delta, TMS int. standard): 8.66-8.77 (2H, m), 7.71 (1H, d, J=7.8 Hz), 7.32 (1H, dd, J=7.5, 5.1 Hz), 7.14 (2H, d, J=8.7 Hz), 6.65 (2H, d, J=8.4 Hz), 6.33 (1H, s), 4.50 (1H, s), 3.61 (1H, t, J=5.1 Hz), 2.29-2.12 (1H, m), 2.09-1.95 (2H, m), 1.93-1.80 (2H, m), 1.69-1.60 (1H, m). HRMS (+E SI): theoretical for [M+H]$^+$=290.1652. found: 290.1654.

M) Synthesis of 3-(Arylidene)-4,6-ethylene-anabaseines

The following arylidene-ethylene-anabaseines were synthesized using either dl-4,6-ethylene-anabaseine hydrochloride (first compound) or 4(R),6(S)-ethylene-anabaseine hydrochloride (remaining compounds) and a slight molar excess of the appropriate substituted benzaldehyde in acidic ethanol, their free bases being obtained by SG chromatography:

i) Characterization of dl-3-(2,4-Dimethoxybenzylidene)-4,6-ethyleneanabaseine (free base)

$^1$H-NMR (300 MHz, CDCl$_3$, delta, TMS int. standard): 8.68 (1H, dd, J=2.4, 0.9 Hz), 8.61 (1H, dd, J=4.8, 1.5 Hz), 7.75 (1H, dt, J=7.5, 1.5 Hz), 7.31 (1H, ddd, J=7.8, 5.1, 0.9), 7.24 (1H, dd, J=8.4, 0.6 Hz), 6.55 (1H, s), 6.50 (1H, dd, J=8.4, 2.7 Hz), 6.43 (1H, d, J=2.4 Hz), 4.52-4.47 (1H, m), 3.47 (1H, t, J=5.4 Hz), 2.28-2.13 (1H, m), 2.07-1.95 (2H, m), 1.92-1.80 (2H, m), 1.67-1.59 (1H, m). $^{13}$C-NMR (75 MHz, CDCl$_3$, delta, TMS int. standard): 165.4, 161.0, 158.7, 148.4, 149.3, 139.7, 136.2, 135.7, 130.4, 127.8, 122.8, 117.5, 104.0, 98.2, 60.2, 55.38, 55.36, 36.4, 36.3, 23.6, 31.2.

ii) Characterization of 3-(4-Hydroxy-3-methoxycinnamylidene)-4(R),6(S)-ethyleneanabaseine (free base)

$^1$H-NMR (300 MHz, CDCl$_3$, delta, TMS int. standard): 8.65-8.60 (2H, m), 7.71 (1H, dt, J=7.5, 1.8 Hz), 7.33 (1H, dd, J=7.5, 4.8 Hz), 7.05-6.93 (2H, m), 6.92-6.84 (2H, m), 6.56

(1H, d, J=15.3 Hz), 6.14 (1H, d, J=11.4 Hz), 4.55 (1H, m), 3.92 (3H, s), 3.54 (1H, t, J=4.8), 2.31-2.00 (2H, m), 1.98-1.81 (2H, m), 1.75-1.64 (2H, m).

iii) Characterization of 3-(5-Acetoxyfurfurylidene)-4 (R),6(S)-ethyleneanabaseine (free base)

$^1$H-NMR (300 MHz, CDCl$_3$, delta, TMS int. standard): 8.65-8.60 (2H, m), 7.70 (1H, dt, J=8.1, 2.1 Hz), 7.32 (1H, ddd, J=7.8, 4.8, 0.9 Hz), 6.44 (1H, d, J=3.3 Hz), 6.38 (1H, d, J=3.3 Hz), 6.15 (1H, s), 4.59-4.54 (1H, m), 3.91 (1H, t, J=4.8 Hz), 2.25-2.12 (1H, m), 2.11-1.98 (1H, m), 1.95-1.82 (2H, m), 1.79-1.63 (2H, m).

iv) Characterization of 3-(Benzo[b]thiophen-2-ylidene)-4(R),6(S)-ethyleneanabaseine (free base)

$^1$H-NMR (300 MHz, CDCl$_3$, delta, TMS int. standard): 8.69-8.64 (2H, m), 7.83-7.70 (3H, m), 7.39-7.30 (3H, m), 7.30-7.24 (1H, m), 6.64 (1H, s), 4.65-4.59 (1H, m), 3.96 (1H, t, J=5.4 Hz), 2.36-2.21 (1H, m), 2.19-2.02 (1H, m), 2.01-1.87 (2H, m), 1.87-1.69 (2H, m).

II. Biological Examples

The practice of the present invention employs, unless otherwise indicated, conventional techniques of molecular biology (including recombinant techniques), microbiology, cell biology, biochemistry, pharmacology, and immunology, which are well within the purview of the skilled artisan.

a). Measurement of Compound Binding to α7 and α4β2 Receptors

Whole male Sprague-Dawley rat brains (Pel-Freeze Biologicals, Rogers, Ariz.) were homogenized with a 30 ml Wheaton (location) glass homogenizing tube and pestle in binding saline (120 mM NaCl, 5 mM KCl, 2 mM CaCl$_2$, 1 mM MgCl$_2$, 50 mM Tris-TrisHCl buffer, pH 7.4). After the homogenate was centrifuged at 11,000 rpm (convert to ×G) for a 10 min, the resulting pellet was resuspended in fresh binding saline and homogenized and centrifuged again. A protein assay (BCA, Pierce, Rockford, Ill.) was then performed to obtain the protein concentration of the rat brain membranes contained in the pellet, which was stored at −85° C. before use.

Radioligands used in the displacement binding assays were obtained from Perkin Elmer Life and Analytical Sciences (Boston, Mass.). $^3$H-Cytisine was used to selectively bind to alpha4beta2 nAChRs and $^{125}$I-α-bungarotoxin (α-Btx) for alpha7 nAChRs. $^3$H-Cytisine (34 Ci/mmol) experiments were performed according to Flores et al. (1992) with a few minor alterations, specifically that the incubation time was increased to four hours at 4° C. to assure binding equilibrium. The $^{125}$I-α-Btx (136 Ci/mmol) experiments involved 37° C. incubation for three hours to assure equilibration. Both radioligands were generally tested at final concentrations of 1 nM. Membranes at the above mentioned concentrations were suspended in binding saline containing 2 mg/ml of bovine serum albumin (Sigma, St. Louis, Mo.) to reduce non-specific binding. For each radioligand, nonspecific binding was measured in the presence of a final concentration of 1 mM (S)-nicotine hydrogen tartrate salt (Sigma, St. Louis, Mo.). After incubation, radioligand bound to membranes in 48 tubes was rapidly collected by vacuum filtration using a Brandel cell harvester (Gaithersburg, Md.) and Whatman GF/C glass fiber filters that were pre-soaked in 0.5% polyethylenimine for 45 minutes to reduce nonspecific binding. The radiolabeled membranes were rapidly washed three times with 3 ml ice-cold binding saline to separate bound from free radioligand. Filters containing $^3$H-cytisine bound membranes were placed in 20 ml scintillation tubes and suspended in 8 mls of 30% Scintisafe scintillation fluid (Fisher), then counted in a Beckman LS-6500 liquid scintillation counter (Fullerton, Calif.). Filters containing $^{125}$I-α-Btx bound membranes were placed in 4 ml scintillation vials and counted in a Beckman 5500B gamma counter (Fullerton, Calif.).

Displacement assay binding data were analyzed using GraphPad Prism software (San Diego, Calif.). The mean counts per minute values for each concentration of a given compound concentration were obtained from 4 replicates. The data were fitted to a sigmoidal concentration response curve from which the Hill slope (n) and IC$_{50}$ (X) values were estimated:

$$Y = \text{Bottom} + (\text{Top} - \text{Bottom})/(1 + 10^{(Log\ IC50-X)n})$$

Here, Top=maximal specific binding of radioligand at the top of the curve and Bottom=minimum specific binding observed at high concentrations of the displacing ligand. The IC$_{50}$ value and the K$_d$ value for the radioligand (0.32 nM for $^{125}$I-α-Btx), previously determined using the same nAChR-containing membrane, were then used to calculate the equilibrium dissociation constant (K$_i$) value of the displacing ligand using the Cheng Prusoff equation (K$_i$=IC$_{50}$/(1+(radioligand)/K$_d$). The alpha7 binding selectivity of each compound shown in Table 1 was estimated by dividing the Ki for alpha4beta2 binding by the Ki for alpha7 binding. The alpha7 binding selectivity of each compound relative to 3-(2,4-dimethoxy benzylidene)-anabaseine (DMXBA) (Table 1) was calculated by dividing the Ki for alpha4beta2 binding by the Ki for alpha7 binding and then dividing this product by the measured alpha7 selectivity of DMXBA (1.95 reported in Table 3 of Kem et al., 2004 Mol. Pharmacol. 65, page 62).

b). Results and Discussion

The binding affinities of the synthesized compounds for the two major rat brain nAChRs are shown in Table 1. Whereas anabaseine (compound 1) displayed almost a 4-fold lower binding affinity (higher Ki) for rat α7 nAChRs (Selectivity factor=0.26), DMXB-anabaseine (compound 2) displayed slightly higher affinity for the α7 nAChR relative to the alpha4beta2 nAChR (Selectivity factor=1.91). In a study of 45 3-(benzylidene)-anabaseines that did not include any of the compounds claimed in this patent application, the average α7 nAChR selectivity was 1.8 (Slavov et al., 2010).

3-(DMXB)-4(R),6(S)-EA (Compound 12 in Table 1) displayed much higher affinity (lower K$_i$) for the α7 receptor than for the α4β2 receptors, displaying the highest binding selectivity (Selectivity factor=13) of the related compounds in Table 1. The enantiomer of this compound, 3-(DMXB)-4 (S),6(R)-EA (Compound 13 in Table 1), displayed an exceptionally low affinity (K$_i$, 4,400 nM) for the α7 receptor, so it is relatively selective for the α4β2 receptor.

Also shown in Table 1, 3-(4AminoB)-4(R),6(S)-EA (Compound 16) demonstrates a high alpha7 affinity as well as a high alpha7/alpha4beta2 selectivity (Selectivity factor=9.9).

The singly methylated (4-methyl- and 6-methyl-DMXB-anabaseines) displayed higher affinities for the alpha7 receptor than for the alpha4beta2 receptor (Table 1). The affinity of 3-(DMXB)-4(R)-methyl-anabaseine (Compound 4) was significantly higher than that of the 3-(DMXB)-4(S)-methyl-anabaseine (compound 5). The 3-(DMXB) 6(S)-methyl-anabaseine (compound 8) affinity was significantly higher than for 3-(DMXB)-6(R)-methyl-anabaseine (compound 9). However, their alpha7 selectivities were inferior to that of 3-(DMXB)-4(R),6(S)-ethylene-anabaseine.

When these two preferred methyl enantiomers were present in the same anabaseine molecule, it also showed higher affinity than DMXB-anabaseine for α7 and better α7 selectivity relative to α4β2 (compound 10). However, the improvement was not as great as would be expected, assuming that the two substitution effects are additive (Table 1).

In brief, the results demonstrated that certain compounds of the invention have an increased affinity for the alpha7 receptor without increased affinity for the other pro-cognitive nAChR (such as, α4β2). Thus, the alpha7 receptor can be stimulated at lower compound concentrations than would be likely to inhibit α4β2 nAChRs, thus providing a high level (>10-fold) in alpha7 nAChR binding selectivity.

Also, certain compounds of the invention display excellent α4β2 nAChR selectivity and thus may be useful as a α4β2 nAChR antagonist in the chronic treatment of nicotine addiction or acute seizures resulting from accidental tobacco, nicotine or related nicotinic compound (including anabaseines) exposures.

Application No.: PCT/US2006/022136, filed Jun. 7, 2006, which claims the benefit of U.S. Provisional Application Ser. No. 60/688,216, the disclosures of which are hereby incorporated herein in their entireties by reference.

All patents and publications mentioned in this specification are herein incorporated by reference to the same extent as if each independent patent and publication was specifically and individually indicated to be incorporated by reference.

REFERENCES

The following documents are cited herein.

Herscovici, J., Egron, M-J., and Antonakis, K. (1982). New Oxidative Systems for Alcohols: Molecular Sieves with Chromium(VI) Reagents. J. Chem. Soc. Perkin Trans. I, 1967-1973.

Kawamura, M. and Ogasawara, K. 1995). Enantio- and Stereocontrolled Syntheses of (−)-Semburin, (+)-N-Benzoylmeroquinene Aldehyde, (−)-Antirhine, and (+)-Isocorynantheol from Common (+)-Norcamphor. Tetrahedron Letters 36, 3369-3372.

Kem, W. R., Mahnir, V. M., Prokai, L., Papke, R. M., Cao, X. F., LeFrancois, S., Wildeboer, K., Porter-Papke, J., Prokai-Tatrai, K., and Soti, F. (2004). Hydroxy metabolites of the Alzheimer's drug candidate DMXBA (GTS-21): Their interactions with brain nicotinic receptors, and brain penetration. Mol. Pharmacol. 65, 56-67.

Krow, G. R., Cheung, 0. H., Hu, Z., and Lee, Y. B. (1996). Regioselective Functionalization. 6. Migratory Preferences in Hydroxylamine-O-sulfonic Acid and Schmidt Rearrangements of 7-Substituted Norcamphors. J. Org. Chem. 61, 5574-5580.

TABLE 1

Rat Brain nAChR Binding of Anabaseines (A) and the Bicyclic 4,6-Ethylene-Anabaseines (EA)

| Compound (Cpd) # | Cpd Name (Abbrev.) | α7 Receptor Rat Ki (nM) | α4β2 Receptor Rat Ki (nM) | α7/α4β2 Selectivity | Enantiomeric Selectivity |
|---|---|---|---|---|---|
| 1 | A | 290 | 76 | 0.26 | NA |
| 2 | 3-(DMXB)-A | 130 | 253 | 1.91 | NA |
| 3 | 3-(4OHB)-A | 360 | 450 | 1.2 | NA |
| 4 | 3-(DMXB)-4(R)-Me-A | 62 | 153 | 2.5 | 2.0 |
| 5 | 3-(DMXB)-4(S)-Me-A | 125 | 191 | 1.5 | |
| 6 | 3-(DMXB)-5(R)-Me-A | 220 | ND | — | 6.8 |
| 7 | 3-(DMXB)-(S)-Me-A | 1,500 | ND | — | |
| 8 | 3-(DMXB)-6(S)-Me-A | 208 | 588 | 2.8 | 3.3 |
| 9 | 3-(DMXB)-6(R)-Me-A | 401 | 344 | 0.86 | |
| 10 | 3-(DMXB)-4(R)Me-6(S)Me-A | 37.6 | 49.8 | 1.3 | 11 |
| 11 | 3-(DMXB)-4(S)Me-6(R)Me-A | 409 | 610 | 1.5 | |
| 12 | 3-(DMXB)-4(R),6(S)-EA | 16.4 | 219 | 13 | 270 |
| 13 | 3-(DMXB)-4(S),6(R)-EA | 4,400 | 347 | 0.079 | |
| 14 | 3-(4OHB)-4(R),6(S)-EA | 34.1 | 72.5 | 2.1 | |
| 15 | 3-(4AminoB)-6(S)Me-A | 73.0 | 314 | 4.3 | NA |
| 16 | 3-(4AminoB)-4(R),6(S)-EA | 3.43 | 34.1 | 9.9 | NA |

[DMXB = 2,4-Dimethoxy Benzylidene; ND = Not Determined; NA = Not Applicable]

Those skilled in the art will recognize, or be able to ascertain using no more than routine experimentation, many equivalents of the specific embodiments of the invention described herein. Such equivalents are intended to be encompassed by the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to U.S. patent application Ser. No. 11/921,832, which is the U.S. national phase application, pursuant to 35 U.S.C. §371, of International Patent Lattanzi, A., Iannece, P., and Scettri, A. (2004). Synthesis of a renewable hydroperoxide from (+)-norcamphor: influence of steric modifications of the bicyclic framework on asymmetric sulfoxidation. Tetrahedron: Asymmetry 15, 1779-1785.

Slavov, S. H., Radzvilovits, M., LeFrancois, S., Stoyanova-Slavova, I. B., Soti, F., Kem, W. R., Katrizky, A. R. (2010) A computational study of the binding of 3-(arylidene) anabaseines to two major brain nicotinic acetylcholine receptors and to the acetylcholine binding protein. Eur. J. Med. Chem. 45, 2433-2446.

We claim:

1. A compound of Formula (I):

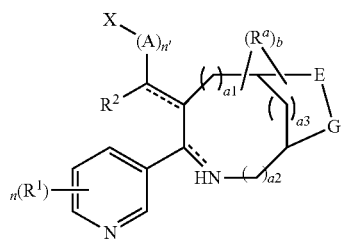

Formula (I)

wherein

------, independently, stands for a single bond or a double bond;

$R^1$, on each occurrence, independently is $(C_1-C_3)$alkyl, hydroxy$(C_1-C_3)$alkyl, $(C_1-C_3)$alkoxy, cyano, halogen, aryl-O—, aryl, or a 5- to 6-membered heteroaryl; or two $R^1$ groups, together with the bonds they are attached to, form a 5 to 8 membered cyclic ring;

n is 0, 1, 2, 3, or 4;

Each of a1, a2, and a3 is 0 or 1, wherein a1, and a2, are 0, and a3 is 1;

$R^2$ is hydrogen, $(C_1-C_3)$alkyl, hydroxy$(C_1-C_3)$alkyl, or $(C_1-C_3)$alkoxy;

E and G, each independently, are $(C_2)$alkylene;

A is a bond or

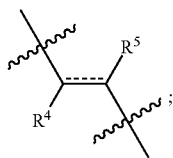

;

n' is 0, 1, or 2;

$R^4$ and $R^5$, on each occurrence, independently are hydrogen, $(C_1-C_3)$alkyl, hydroxy$(C_1-C_3)$alkyl, or $(C_1-C_3)$alkoxy;

X is aryl or heteroaryl, wherein said aryl and said heteroaryl are optionally substituted by one to five $R^3$ groups and/or one $R^c$ group;

$R^3$, on each occurrence, independently is hydrogen, halogen, $(C_1-C_3)$alkyl-C(O)O—, $(C_1-C_3)$alkyl-C(O)—, $(C_1-C_3)$alkyl-C(O)N($R^6$), N($R^6$)$_2$—, $(R^6)_2$NC(O)—, $(R^6)_2$N$(C_1-C_5)$alkoxy, $(R^6)_3$N$^\oplus(C_1-C_5)$ alkoxy, hydroxyl, cyano, a sugar moiety or derivative thereof, $(C_1-C_3)$alkoxy optionally substituted by one or more same or different halogen or thio groups, or $(C_1-C_3)$alkyl optionally substituted by one or more same or different halogen or hydroxyl groups;

$R^6$, on each occurrence, independently is hydrogen, $(C_1-C_3)$alkyl, hydroxy$(C_1-C_3)$alkyl, or $(C_1-C_3)$alkoxy;

$R^a$ on each occurrence, independently is hydrogen, $(C_1-C_3)$ alkyl, hydroxy$(C_1-C_3)$alkyl, $(C_1-C_3)$alkoxy, cyano, halogen, aryl, or aryl-O—;

$R^c$ is hydrogen, $(C_1-C_5)$alkoxy, or $(C_1-C_5)$alkyl, wherein said $(C_1-C_5)$alkoxy and said $(C_1-C_5)$alkyl are optionally substituted by one or more same or different substituents selected from the group of hydroxyl, $(C_1-C_3)$alkoxy, halogen, and thio; and b is 0, 1, 2, 3, or 4;

or a pharmaceutically acceptable salt, solvate, hydrate, clathrate, polymorph, stereoisomer, enantiomer, or combination thereof.

2. The compound of claim 1, wherein said compound is of Formula (IA)

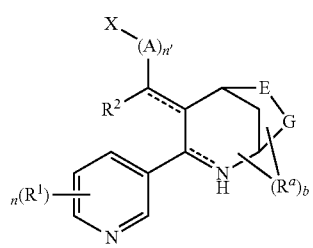

Formula (IA)

wherein

------, independently, stands for a single bond or a double bond;

$R^1$, on each occurrence, independently is $(C_1-C_3)$alkyl, hydroxy$(C_1-C_3)$alkyl, $(C_1-C_3)$alkoxy, cyano, halogen, aryl-O—, aryl, or a 5- to 6-membered heteroaryl; or two $R^1$ groups, together with the bonds they are attached to, form a 5 to 8 membered cyclic ring;

n is 0, 1, 2, 3, or 4;

$R^2$ is hydrogen, $(C_1-C_3)$alkyl, hydroxy$(C_1-C_3)$alkyl, or $(C_1-C_3)$alkoxy;

E and G, each independently, are $(C_2)$alkylene;

A is a bond or

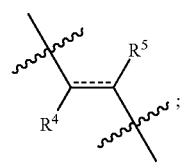

;

n' is 0 or 1;

$R^4$ and $R^5$, on each occurrence, independently are hydrogen, $(C_1-C_3)$alkyl, hydroxy$(C_1-C_3)$alkyl, or $(C_1-C_3)$alkoxy;

X is aryl or heteroaryl, wherein said aryl and said heteroaryl are optionally substituted by one to five $R^3$ groups and/or one $R^c$ group;

$R^3$, on each occurrence, independently is hydrogen, halogen, $(C_1-C_3)$alkyl-C(O)O—, $(C_1-C_3)$alkyl-C(O)N($R^6$), N($R^6$)$_2$—, $(R^6)_2$NC(O)—, $(R^6)_2$N$(C_1-C_5)$alkoxy, $(R^6)_3$N$^\oplus(C_1-C_5)$ alkoxy, hydroxyl, a sugar moiety or derivative thereof, $(C_1-C_3)$alkoxy optionally substituted by one or more same or different halogen or thio groups, or $(C_1-C_3)$alkyl optionally substituted by one or more same or different halogen or hydroxyl groups; and R⁶, on each occurrence, independently is hydrogen, (C₁-C₃)alkyl, hydroxy(C₁-C₃)alkyl, or (C₁-C₃)alkoxy;

Rᵃ on each occurrence, independently is hydrogen, (C₁-C₃) alkyl, hydroxy(C₁-C₃)alkyl, (C₁-C₃)alkoxy, cyano, halogen, aryl, or aryl-O—;

Rᶜ is hydrogen, or (C₁-C₅)alkyl optionally substituted by one or more same or different substituent(s) selected from the group of hydroxyl, (C₁-C₃)alkoxy, halogen, and thio; and b is 0, 1, 2, 3, or 4;

or a pharmaceutically acceptable salt, solvate, hydrate, clathrate, polymorph, stereoisomer, enantiomer, or combination thereof.

3. The compound of claim 2, wherein said compound is a compound of Formula (IIa):

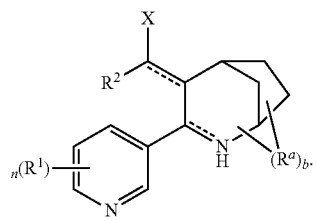

Formula (IIa)

4. The compound of claim 3, wherein b is 0.

5. The compound of claim 4, wherein said compound is a compound of Formula (III-A)

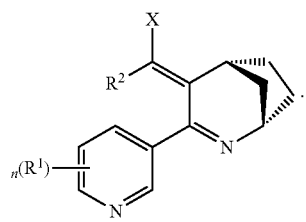

Formula (III-A)

6. The compound of claim 5, wherein n is 0, and R³ is amino, (C₁-C₃)alkoxy or hydroxyl.

7. The compound of claim 6, wherein said compound is

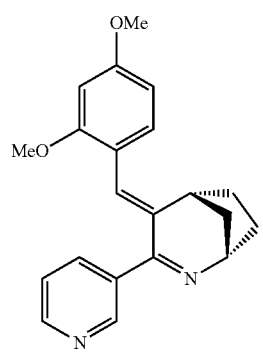 [SMILES: COc1ccc(/C=C2/C(c3cccnc3)=N[C@H]3CC[C@@H]2C3)c(OC)c1]

(1S,5R,E)-4-(2,4-dimethoxybenzylidene)-3-(pyridin-3-yl)-2-azabicyclo[3.2.1]oct-2-ene ("3-(DMXB)-4(R),6(S)-EA");

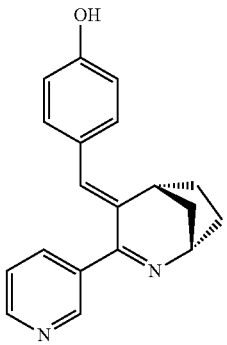 [SMILES: Oc1ccc(/C=C2/C(c3cccnc3)=N[C@H]3CC[C@@H]2C3)cc1]

4-((E)-((1S,5R)-3-(pyridin-3-yl)-2-azabicyclo[3.2.1]oct-2-en-4-ylidene)methyl)phenol ("3-(4OHB)-4(R),6(S)-EA"); or

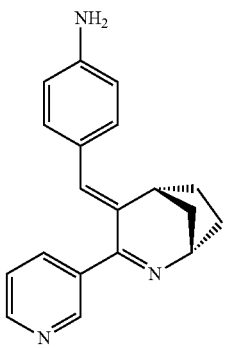 [SMILES: Nc1ccc(/C=C2/C(c3cccnc3)=N[C@H]3CC[C@@H]2C3)cc1]

3-(4-Aminobenzylidene)-4(R),6(S)-ethylene-anabaseine ("3-(4AminoB)-4(R),6(S)-EA").

8. The compound of claim 4, wherein said compound is a compound of Formula (III-B)

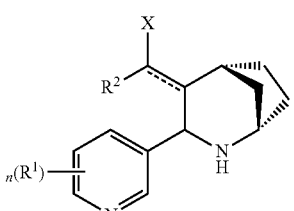

Formula (III-B)

wherein ----- stands for a single bond or a double bond.

9. The compound of claim 4, wherein said compound is a compound of Formula (III-C)

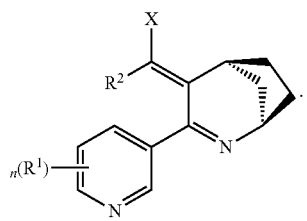

Formula (III-C)

10. The compound of claim 9, wherein said compound is

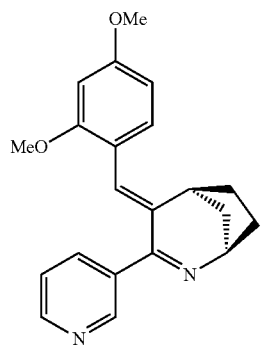 [SMILES: COc1ccc(/C=C2/C(c3cccnc3)=N[C@@H]3CC[C@H]2C3)c(OC)c1]

(1R,5S,E)-4-(2,4-dimethoxybenzylidene)-3-(pyridin-3-yl)-2-azabicyclo[3.2.1]oct-2-ene ("3-(DMXB)-4(S),6(R)-EA").

11. The compound of claim 3, wherein said compound is a compound of Formula (III-D):

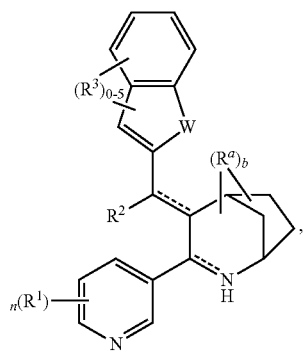

Formula (III-D)

wherein W is O or S, and ----, independently, stands for a single bond or a double bond.

12. The compound of claim 3, wherein said compound is a compound of Formula (III-E):

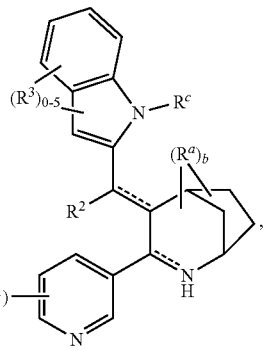

Formula (III-E)

wherein
----, independently, stands for a single bond or a double bond;
$R^c$ is hydrogen, or $(C_1-C_5)$alkyl optionally substituted by one or more same or different substituent(s) selected from the group of hydroxyl, $(C_1-C_3)$alkoxy, and halogen; and
$R^1$, $R^2$, $R^3$, $R^a$, b, and n are defined in claim 2.

13. The compound of claim 2, wherein said compound is a compound of Formula (IIb):

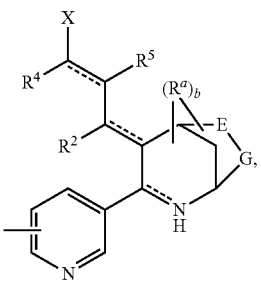

Formula (IIb)

wherein ----, $R^1$, $R^2$, $R^4$, $R^5$, $R^a$, E, G, X, n, and b are defined in claim 2.

14. The compound of claim 2, wherein said compound is of Formula (IIc)

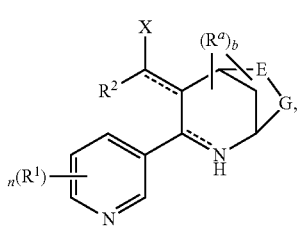

Formula (IIc)

wherein, $R^1$, $R^2$, $R^a$, X, E, G, n, and b are defined in claim 2.

* * * * *